US008535881B2

(12) United States Patent
Schneider (10) Patent No.: US 8,535,881 B2
(45) Date of Patent: Sep. 17, 2013

(54) HIGH SPEED PARALLEL MOLECULAR NUCLEIC ACID SEQUENCING

(75) Inventor: Thomas D. Schneider, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 478 days.

(21) Appl. No.: 12/886,686

(22) Filed: Sep. 21, 2010

(65) Prior Publication Data

US 2011/0008794 A1  Jan. 13, 2011

Related U.S. Application Data

(60) Continuation of application No. 12/196,139, filed on Aug. 21, 2008, now abandoned, which is a continuation of application No. 11/204,367, filed on Aug. 12, 2005, now abandoned, which is a division of application No. 10/070,053, filed as application No. PCT/US00/23736 on Aug. 29, 2000, now Pat. No. 6,982,146.

(60) Provisional application No. 60/151,580, filed on Aug. 30, 1999.

(51) Int. Cl.
| C12Q 1/68 | (2006.01) |
| C12P 19/34 | (2006.01) |
| C07H 21/02 | (2006.01) |
| C07H 21/04 | (2006.01) |

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| 4,711,955 A | 12/1987 | Ward et al. |
| 4,793,705 A | 12/1988 | Shera |

(Continued)

FOREIGN PATENT DOCUMENTS

| WO | WO 97/30366 | 8/1997 |
| WO | WO 97/40191 | 10/1997 |

(Continued)

OTHER PUBLICATIONS

Song, L. et al., Biophys. J., vol. 70, pp. 2959-2968 (1996).*

(Continued)

*Primary Examiner* — Teresa E Strzelecka
(74) *Attorney, Agent, or Firm* — Klarquist Sparkman, LLP (57) ABSTRACT

A method and device is disclosed for sequencing of nucleic acid molecules. A nucleic acid molecule is exposed to a polymerase in the presence of nucleotides. The polymerase carries a donor fluorophore, and each type of nucleotide carries a distinguishable acceptor fluorophore characteristic of the particular type of nucleotide. As the polymerase incorporates individual nucleic acid molecules into a complementary strand, a laser continuously irradiates the donor fluorophore, at a wavelength that causes it to emit an emission signal. The emission signal from the polymerase can stimulate any of the donor fluorophores (but not acceptor fluorophores), so that as a nucleotide is added, the acceptor fluorophore emits a signal associated with the type of nucleotide added to the complementary strand. The series of emission signals from the acceptor fluorophores is detected, and correlated with a sequence of nucleotides that correspond to the sequence of emission signals.

19 Claims, 2 Drawing Sheets

(56) References Cited

U.S. PATENT DOCUMENTS

| | | | |
|---|---|---|---|
| 4,917,462 A | 4/1990 | Lewis et al. | |
| 4,962,037 A | 10/1990 | Jett et al. | |
| 5,017,009 A | 5/1991 | Schutt et al. | |
| 5,047,519 A | 9/1991 | Hobbs, Jr. et al. | |
| 5,064,754 A | 11/1991 | Mills | |
| 5,105,305 A | 4/1992 | Betzig et al. | |
| 5,124,247 A | 6/1992 | Ansorge | |
| 5,151,507 A | 9/1992 | Hobbs, Jr. et al. | |
| 5,221,518 A | 6/1993 | Mills | |
| 5,242,796 A | 9/1993 | Prober et al. | |
| 5,306,618 A | 4/1994 | Prober et al. | |
| 5,332,666 A | 7/1994 | Prober et al. | |
| 5,354,985 A | 10/1994 | Quate | |
| 5,360,523 A | 11/1994 | Middendorf et al. | |
| 5,389,779 A | 2/1995 | Betzig et al. | |
| 5,405,747 A | 4/1995 | Jett et al. | |
| 5,470,710 A | 11/1995 | Weiss et al. | |
| 5,547,835 A | 8/1996 | Köster | |
| 5,556,790 A | 9/1996 | Pettit | |
| 5,614,386 A | 3/1997 | Metzker et al. | |
| 5,625,048 A | 4/1997 | Tsien et al. | |
| 5,654,176 A | 8/1997 | Smith | |
| 5,661,028 A | 8/1997 | Foote | |
| 5,674,743 A | 10/1997 | Ulmer | |
| 5,707,804 A | 1/1998 | Mathies et al. | |
| 5,763,594 A | 6/1998 | Hiatt et al. | |
| 5,777,079 A | 7/1998 | Tsien et al. | |
| 5,780,232 A | 7/1998 | Arlinghaus et al. | |
| 5,800,996 A | 9/1998 | Lee et al. | |
| 5,814,454 A | 9/1998 | Ju | |
| 5,821,058 A | 10/1998 | Smith et al. | |
| 5,866,336 A | 2/1999 | Nazarenko et al. | |
| 6,210,896 B1 | 4/2001 | Chan | |
| 6,682,893 B2 | 1/2004 | Taylor et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 2001/0008766 A1 | 7/2001 | Daunert et al. | |
| 2002/0164629 A1 | 11/2002 | Quake et al. | |
| 2003/0064366 A1 | 4/2003 | Hardin et al. | |
| 2003/0134807 A1 | 7/2003 | Hardin et al. | |

FOREIGN PATENT DOCUMENTS

| | | |
|---|---|---|
| WO | WO 98/33939 | 8/1998 |
| WO | WO 99/05315 | 2/1999 |
| WO | WO 00/53805 | 9/2000 |
| WO | WO 00/70073 | 11/2000 |
| WO | WO 01/16375 A2 | 3/2001 |
| WO | WO 02/04680 A2 | 1/2002 |
| WO | WO 2004/074503 A2 | 9/2004 |

OTHER PUBLICATIONS

Allen et al., "Resonance Energy Transfer Measurements Between Substrate Binding Sites Within the Large (Klenow) Fragment of *Escherichia coli* DNA Polymerase I," *Biochem.* 28:9586-9593 (1989).

Baubet et al., "Chimeric Green Fluorescent Protein-Aequorin as Bioluminiscent $Ca^{2+}$ Reporters at the Single-Cell Level," *Proc. Natl. Acad. Sci. USA* 97:7260-7265 (2000).

Bentley, "Whole-Genome Re-Sequencing," *Curr. Opin. Genetics. Dev.* 16:545-552, 2006.

Braslaysky et al., "Sequence information can be obtained from single DNA molecules," *Proc. Natl. Acad. Sci.* 100:3960-3964 (2003).

Burns et al., "Studies in Fluorescence Histochemistry. X. Optimum Conditions of the Acetic Anhydride-Salicylhydrazide-Zinc (or Fluorescent Ketone) Technique for Demonstrating C-Terminal Carboxyl Groups of Proteins," *Histochemie* 26:279-288 (1971).

Clegg, "Fluorescence Resonance Energy Transfer and Nucleic Acids," *Methods in Enzymol.* 211:353-388 (1992).

Delgrave et al., "Red-Shifted Excitation Mutants of the Green Fluorescent Protein," *Bio/Tech.* 13:151-154 (1995).

Elcin, "Encapsulation of urease enzyme in xanthan-alginate spheres," *Biomaterials*, 16:1157-1161 (1995).

Ehrig et al., "Green-Fluorescent Protein Mutants with Altered Fluorescence Excitation Spectra," *FEBS Lett.* 367:163-166 (1995).

Fang et al., Imaging Single Fluorescent Molecules at the Interface of an Optical Fiber Probe by Evanescent Wave Excitation, *Anal. Chem.* 71:3101-3105 (1999).

Funatsu et al., "Imaging of Single Fluorescent Molecules and Individual ATP Turnovers by Single Myosin Molecules in Aqueous Solution," *Nature* 374:555-559 (1995).

Furey et al., "Use of Fluorescence Resonance Energy Transfer to Investigate the Conformation of DNA Substrates Bound to the Klenow Fragment," *Biochemistry* 37:2979-2990 (1998).

Gordon et al., "Quantitative Fluorescence Resonance Energy Transfer Measurements Using Fluorescence Microscopy," *Biophys. J.* 74:2702-2313 (1998).

Ha et al., Probing the Interaction Between Two Single Molecules: Fluorescence Resonance Energy Transfer Between a Single Donor and a Single Acceptor, *Proc. Natl. Acad. Sci. USA* 93:6264-6268 (1996).

Harada et al., "Mechanochemical Coupling in Actomyosin Energy Transduction Studied by in Vitro Movement Assay," *J. Mol. Biol.* 216:49-68 (1990).

Harms et al., "Single-Molecule Anisotrophy Imaging," *Biophys. J.* 77:2864-2870 (1999).

Heyduk et al., "Architecture of a Complex Between the $\sigma^{70}$ Subunit of *Escherichia coli* RNA Polymerase and the Nontemplate Strand Oligonucleotide," *J. Biol. Chem.* 274:3315-3322 (1999).

Heyduk et al., "Thiol-Reactive, Luminescent Europium Chelates: Luminescence Probes for Resonance Energy Transfer Distance Measurements in Biomolecules," *Anal. Biochem.* 248:216-227 (1997).

Hung et al., "Cyanine Dyes with High Absorption Cross Section as Donor Chromophores in Energy Transfer Primers," *Anal. Biochem.* 243:15-27 (1996).

Inouye et al.,"*Aequorea* Green Fluorescent Protein. Expression of the Gene and Fluorescence Characteristics of the Recombinant Protein," *FEBS Lett.* 341:277-280 (1994).

Itakura et al., "Force-Generating Domain of Myosin Motor," *Biochem. Biophys. Res.Comm.* 196:1504-1510 (1993).

Karger et al., "Multiwavelength Fluorescence Detection for DNA Sequencing Using Capillary Electrophoresis," *Nucleic Acids Res.* 19:4955-4962 (1991).

Kheterpal et al., "Capillary Array Electophoresis DNA Sequencing," *Analy. Chem. News & Features*, pp. 31A-37A (1999).

Kitamura et al., "A Single Myosin Head Moves Along an Actin Filament with Regular Steps of 5.3 Nanometres," *Nature* 397:129-134 (1999).

Kumar et al., "Silanized Nucleic Acids: A General Platform for DNA Immobilization," *Nucleic Acids Res.* 28:e71 (2000).

Lemon et al., "Localization of Bacterial DNA Polymerase: Evidence for a Factory Model of Replication," *Science* 282:1516-1519 (1998).

Mazzola et al., "Imaging Biomolecule Arrays by Atomic Force Microscopy," *Biophys. J.* 68:1653-1660 (1995).

Mitra et al., "Fluorescence Resonance Energy Transfer Between Blue-Emitting and Red-Shifted Excitation Derivatives of the Green Fluorescent Protein," *Gene* 173:13-17 (1996).

Müller, et al., "A Strategy for the Chemical Synthesis of Nanostructures," *Science* 268:272-273 (1995).

Park et al., "Block Copolymer Lithography: Periodic Arrays of $\sim 10^{11}$ Holes in 1 Square Centimeter," *Science* 276:1401-1404 (1997).

Park et al., "Green Fluorescent Protein as a Signal for Protein-Protein Interactions," *Protein Science* 6:2344-2349 (1997).

Pierce et al., "Imaging Individual Green Fluorescent Proteins," *Nature* 388:338 (1997).

Selvin and Hearst, "Luminescence Energy Transfer Using a Terbium Chelate: Improvements on Fluorescence Energy Transfer," *Proc. Natl. Acad. Sci. USA* 91:10024-10028 (1994).

Sinclair, "Sequence or Die—Automated Instrumentation for the Genome Era," *The Scientist*, pp. 18-20, Apr. 12, 1999.

Szöllósi et al., "Application of Fluorescence Resonance Energy Transfer in the Clinical Laboratory: Routine and Research," *Cytometry* 34:159-179 (1998).

Travis, "Physics Festival Brightens Rainy San Jose," *Science* 268:30-31 (1995).

Unger et al., "Single-Molecule Fluorescence Observed with Mercury Lamp Illumination," *Bio Techniques* 27:1008-1014 (1999).

Weiss, "Fluorescence Spectroscopy of Single Biomolecules," *Science* 283:1676-1683 (1999).

\* cited by examiner

HIGH SPEED PARALLEL MOLECULAR NUCLEIC ACID SEQUENCING

CROSS REFERENCE TO RELATED APPLICATIONS

This is a continuation of U.S. application Ser. No. 12/196,139 filed Aug. 21, 2008 now abandoned, which is a continuation of U.S. application Ser. No. 11/204,367, filed Aug. 12, 2005 (abandoned), which is a divisional of U.S. application Ser. No. 10/070,053, filed Jun. 10, 2002, issued as U.S. Pat. No. 6,982,146 on Jan. 3, 2006, which is a §371 national stage of PCT/US00/23736, filed Aug. 29, 2000, which was published in English under PCT Article 21(2), which in turn claims the benefit of U.S. Provisional Application No. 60/151,580, filed Aug. 30, 1999. All applications are incorporated herein in their entirety by reference.

FIELD

This disclosure relates to an automated method for sequencing nucleic acids, such as DNA and RNA, which may be used for research and the diagnosis of disease in clinical applications.

BACKGROUND

Approaches to DNA sequencing over the past twenty years have varied widely. The use of enzymes and chemicals is making it possible to sequence the human genome. However, this effort takes enormous resources.

Until recently, there were only two general sequencing methods available, the Maxam-Gilbert chemical degradation method (Maxam and Gilbert, 1977, *Proc. Natl. Acad. Sci., USA* 74:560), and the Sanger dideoxy chain termination method (Sanger et al., 1977, *Proc. Natl. Acad. Sci., USA* 74:5463). Using the dideoxy chain termination DNA sequencing method, DNA molecules of differing lengths are generated by enzymatic extension of a synthetic primer, using DNA polymerase and a mixture of deoxy- and dideoxy-nucleoside triphosphates. To perform this reaction, the DNA template is incubated with a mixture containing all four deoxynucleoside 5'-triphosphates (dNTPs), one or more of which is labeled with $^{32}P$, and a 2',3'-dideoxynucleoside triphosphate analog (ddNTP). Four separate incubation mixtures are prepared, each containing a different ddNTP analog (ddATP, ddCTP, ddGTP, or ddTTP). The dideoxynucleotide analog is incorporated normally into the growing complementary DNA strand by the DNA polymerase, through their 5' triphosphate groups.

However, because of the absence of a 3'-OH group on the ddNTP, phosphodiester bonds cannot be formed with the next incoming dNTPs. This results in termination of the growing complementary DNA chain. Therefore, at the end of the incubation period, each reaction mixture contains a population of DNA molecules having a common 5' terminus, but varying in length to a nucleotide base specific 3' terminus. These four preparations, with heterogeneous fragments each ending in either cytosine (C), guanine (G), adenine (A) or thymine (T) are separated in four parallel lanes on polyacrylamide gels. The sequence is determined after autoradiography, by determining the terminal nucleotide base at each incremental cleavage in the molecular weight of the electrophoresed fragments.

The Maxam-Gilbert method of DNA sequencing involves the chemical-specific cleavage of DNA. In this method, radiolabeled DNA molecules are incubated in four separate reaction mixtures, each of which partially cleaves the DNA at one or two nucleotides of a specific identity (G, A+G, C or C+T). The resulting DNA fragments are separated by polyacrylamide gel electrophoresis, with each of the four reactions fractionated in a separate lane of the gel. The DNA sequence is determined after autoradiography, again by observing the macromolecular separation of the fragments in the four lanes of the gel.

The use of fluorescent nucleotides has eliminated the need for radioactive nucleotides, and provided a means to automate DNA sequencing. As fluorescent DNA fragments on an electrophoresis gel pass by a detector, the sequential fluorescent signals (which correspond to a fragment ending in a particular nucleotide) are automatically converted into the DNA sequence, eliminating the additional step of exposing the gel to film. Improvements on this general concept have been the subject of several U.S. patents, including U.S. Pat. No. 5,124,247 to Ansorge, U.S. Pat. No. 5,242,796 to Prober et al., U.S. Pat. No. 5,306,618 to Prober et al., U.S. Pat. No. 5,360,523 to Middendorf et al., U.S. Pat. No. 5,556,790 to Pettit, and U.S. Pat. No. 5,821,058 to Smith et al. However, the methods disclosed in these patents still require the inconvenient step of separating the generated DNA fragments by size, using electrophoresis.

There are several disadvantages associated with using electrophoresis for nucleic acid sequencing. Electrophoresis requires macroscopic separation, with the necessity of expensive reagents, long gel preparation time, tedious sample loading, the dangers of exposure to the neurotoxin acrylamide. Macromolecular electrophoretic separation also exposes the technician to high voltage devices, requires prolonged electrophoresis time, produces gel artifacts, and requires calculations to adjust for dye mobilities. Furthermore, sequencing runs only allow for the sequencing of less than 1000 bases at a time, which can be a substantial drawback to the sequencing of long stretches of the genome.

Given the practical drawbacks of electrophoresis, attempts have been made to eliminate this step. Mills, for example, described the use of mass spectrometry to separate the DNA fragments as an alternative to electrophoresis (U.S. Pat. Nos. 5,221,518 and 5,064,754). However, mass spectrometry devices are expensive, and because the method depends on size separation, it has a size resolution limit.

Others have attempted to separate nucleic acid sequences by size using capillary electrophoresis (Karger, *Nucl. Acids Res.* 19:4955-62, 1991). In this method, fused silica capillaries filled with polyacrylamide gel are used as an alternative to slab gel electrophoresis. However, this method is limited by the separation process and requires very high detection sensitivity and wavelength selectivity due to the small sample size.

Melamede (U.S. Pat. No. 4,863,849) and Cheeseman (U.S. Pat. No. 5,302,509) describe DNA sequencing methods which require a complex external liquid pumping system to add and remove necessary reagents. In these "open" systems, which contain the polymerase and the DNA to be sequenced, fluorescent nucleotides are pumped into a reaction chamber and added to the DNA molecule. After the incorporation of a single nucleotide, unincorporated fluorescent dNTPs are removed, leaving behind the DNA and its newly incorporated fluorescent nucleotide. This incorporated nucleotide is detected, its signal converted into a DNA sequence, and the process is repeated until the sequencing is complete. Although these methods can eliminate the electrophoresis step, the addition of nucleotides must be monitored one at a time as they are added to a population of DNA molecules, by continually pumping materials in and out of the reaction chamber.

In another automated process, Jett et al. (U.S. Pat. Nos. 4,962,037 and 5,405,747) uses an exonuclease to sequentially shorten a DNA molecule that is being sequenced. After a complementary DNA strand is synthesized in the presence of fluorescent nucleotides, the exonuclease cleaves individual fluorescent nucleotides from the end of the synthesized DNA molecule. These nucleotides pass through a detector, and the fluorescent signal emitted by each nucleotide is recorded to determine the DNA sequence.

In the methods of Melamede (U.S. Pat. No. 4,863,849) and Cheeseman (U.S. Pat. No. 5,302,509) described above, the addition or release of nucleotides from several DNA molecules is monitored simultaneously. This is sequencing at the macromolecular level, as opposed to sequencing at the molecular level, which involves monitoring the addition or release of nucleotides from a single DNA molecule. A disadvantage of macromolecular sequencing methods is that even though all of the DNA molecules start with identical nucleotides, they may quickly evolve into a mixed population. When using the macromolecular methods, some chains may more efficiently incorporate nucleotides than others, and some DNA may be degraded more slowly or rapidly than others.

To solve this synchronization problem, Jett et al. (U.S. Pat. No. 4,962,037) and Ulmer (U.S. Pat. No. 5,674,743) developed molecular level sequencing systems in which a single fluorescently labeled DNA base is sequentially cleaved from a DNA molecule. The fluorescent signal from each cleaved dNTP is used to determine the DNA sequence. One drawback to these methods, however, is that the DNA molecule which is being sequenced must be held in a stream, which often results in shearing of the DNA, especially at higher flow rates. The sheared DNA molecule can not be accurately sequenced. In addition, only one DNA molecule can be sequenced at a time by this method.

The development of fluorescence resonance energy transfer (FRET) labels for DNA sequencing has been described by Ju (U.S. Pat. No. 5,814,454) and Mathies et al. (U.S. Pat. No. 5,707,804). During FRET, exciting the donor dye with light of a first wavelength releases light of a second wavelength, which in turn excites the acceptor dye(s) to emit light of a third wavelength, which is then detected. These patents disclose the attachment of FRET labels to oligonucleotide primers for sequencing DNA molecules. A drawback of these methods is that there is still a need for size separation (for example using electrophoresis) prior to determining the DNA sequence.

Therefore, there remains a need for a method of sequencing nucleic acids at the molecular scale, that does not require the use of electrophoresis or complex liquid pumping systems, and does not result in the shearing of nucleic acids. In addition, methods that are automated would be particularly useful.

SUMMARY OF THE DISCLOSURE

The present disclosure provides an improved method and device for sequencing nucleic acids. The method allows several nucleic acids to be sequenced simultaneously at the molecular level. In particular examples, the method uses a donor and acceptor class of dyes. This method and device minimize shearing the sample nucleic acids to be sequenced, and can be readily automated.

Herein disclosed is a method of sequencing a sample nucleic acid molecule by exposing the sample nucleic acid molecule to an oligonucleotide primer and a polymerase in the presence of a mixture of nucleotides. The polymerase carries a fluorophore, and each different type of nucleotide (e.g. A, T/U, C or G) carries a fluorophore which emits a signal that is distinguishable from a signal emitted by the fluorophore carried by each of the other types of nucleotides. In particular embodiments the fluorophore on the polymerase is a donor fluorophore and the fluorophore carried on the nucleotides are acceptor fluorophores. The donor fluorophore can be excited by a source of electromagnetic radiation (such as a laser) that specifically excites the donor fluorophore and not the acceptor fluorophores. This excitation induces the donor to emit light at a wavelength that can transfer energy to excite only the acceptor fluorophores that are added to the complementary strand by the polymerase. As the donor fluorophore excites the acceptor, a signal characteristic of the specific nucleotide being added (e.g. A, T/U, C or G) is emitted by the acceptor fluorophore. A series of sequential signals emitted by the added nucleotides is detected, and converted into the complement of the nucleic acid sample. In particular embodiments, the unique emission signal for each nucleotide is generated by luminescence resonance energy transfer (LRET) or fluorescent resonance energy transfer (FRET).

In other embodiments, the nucleic acid is a DNA or RNA molecule, and correspondingly, the polymerase is a DNA or RNA polymerase, if DNA is being sequenced, or reverse transcriptase if RNA is being sequenced. In a further embodiment, the polymerase is a Klenow fragment of DNA polymerase I. In particular embodiments, the polymerase is a GFP-polymerase. In another embodiment, the donor fluorophore is green fluorescent protein (GFP). In particular embodiments, the donor fluorophore, such as GFP, is excited by a laser. In other embodiments, GFP can be excited by a luminescent molecule, for example aequorin.

Alternatively, the donor fluorophore is a luminescent molecule, for example aequorin or europium chelates. In this embodiment, the donor fluorophore does not require excitation by a source of electromagnetic radiation, because the luminescent donor fluorophore is naturally in an excited state.

In yet another embodiment, the acceptor fluorophores are BODIPY® dye, fluorescein, RHODAMINE GREEN™ dye, and OREGON GREEN® dye or derivatives thereof. In particular, the donor fluorophore and one of the acceptor fluorophores comprise a donor/acceptor fluorophore pair selected from the group consisting of the GFP mutant H9-40, tetramethylrhodamine, LISSAMINE™ dye, TEXAS RED® dye and naphthofluorescein.

Also disclosed herein are embodiments in which the polymerase may be fixed to a substrate, for example by a linker molecule that includes a polymerase component and a substrate component. The linker may be selected from the group consisting of streptavidin-biotin, histidine-Ni, S-tag-S-protein, and glutathione-S-transferase (GST). In another embodiment, a nucleic acid may be fixed to a substrate. In particular embodiments the oligonucleotide primer is fixed to a substrate, for example at its 5' end. In yet other embodiments, the sample nucleic acid to be sequenced is fixed to the substrate. In particular embodiments, the sample nucleic acid to be sequenced is fixed to the substrate by its 5' end, 3' end or anywhere in between. In another embodiment, a plurality of polymerases, oligonucleotide primers, or sample nucleic acids are fixed directly or indirectly to the substrate in a predetermined pattern. For example, the polymerases can be deposited into channels which have been etched in an orderly array or by micropipetting droplets containing the polymerases onto a slide, for example either by manually pipetting or with an automated arrayer. In other embodiments, a plurality of sequencing reactions are performed substantially simultaneously, and the signals from the plurality of sequencing reactions detected.

Many different sequencing reactions can be performed substantially simultaneously on a single substrate, in which case signals are detected from each of the sequencing reactions. The unique emission signals are detected with a charged-coupled device (CCD) camera as an example of a detector, which can detect a sequence of signals from a predetermined position on the substrate, and convert them into the nucleic acid sequence. The unique emission signals may be stored in a computer readable medium.

Also disclosed is a substrate to which is attached a GFP-polymerase. In another embodiment, GFP-polymerase contains an affinity tag that attaches the GFP-polymerase to the substrate. In yet another embodiment, the GFP-polymerase is attached to the substrate by a linker.

Other embodiments disclosed herein include a method of sequencing a sample nucleic acid by attaching a polymerase to a substrate, adding the sample nucleic acid with an annealed oligonucleotide to the polymerase, and allowing the sample nucleic acid to bind to the polymerase in the presence of nucleotides for incorporation into a complementary nucleic acid. The polymerase and nucleotides are labeled with donor and acceptor fluorophores that emit a distinguishable signal when a particular type of nucleotide (e.g. A, T/U, C or G) is incorporated into the complementary nucleic acid. A sequence of the distinguishable signals are detected as the nucleotides are sequentially added to the complementary nucleic acid, and the sequence of signals are converted into a corresponding nucleic acid sequence.

Also disclosed herein is a method of sequencing a sample nucleic acid by attaching a sample nucleic acid to a substrate, adding an oligonucleotide primer and allowing the oligonucleotide primer to anneal to the attached sample nucleic acid, adding a polymerase in the presence of nucleotides, and allowing the sample nucleic acid to bind to the polymerase in the presence of nucleotides for incorporation into a complementary nucleic acid. The polymerase and nucleotides are labeled with donor and acceptor fluorophores that emit a distinguishable signal when a particular type of nucleotide (e.g. A, T/U, C or G) is incorporated into the complementary nucleic acid. A sequence of the distinguishable signals is detected as the nucleotides are sequentially added to the complementary nucleic acid, and the sequence of signals are converted into a corresponding nucleic acid sequence. The sample nucleic acid can be attached to a substrate, for example at its 5'- or 3' end, or anywhere in between.

Another embodiment disclosed herein is a method of sequencing a sample nucleic acid by attaching an oligonucleotide primer to a substrate, adding a sample nucleic acid and allowing the oligonucleotide primer to anneal to the sample nucleic acid, adding a polymerase in the presence of nucleotides, and allowing the sample nucleic acid to bind to the polymerase in the presence of nucleotides for incorporation into a complementary nucleic acid. The polymerase and nucleotides are labeled with donor and acceptor fluorophores that emit a distinguishable signal when a particular type of nucleotide (e.g. A, T/U, C or G) is incorporated into the complementary nucleic acid. A sequence of the distinguishable signals is detected as the nucleotides are sequentially added to the complementary nucleic acid, and the sequence of signals is converted into a corresponding nucleic acid sequence.

The present disclosure also includes a device for sequencing a nucleic acid molecule, in which a polymerase (carrying a donor fluorophore), oligonucleotide primer, or sample nucleic acid is attached to a substrate. The device also includes a viewing means to view the polymerase, and a detection means that detects a characteristic signal from an acceptor fluorophore carried by a corresponding nucleotide, as the nucleotide is added to the nucleic acid molecule by the polymerase. An electromagnetic radiation source (such as light of a specified wavelength range) excites the donor fluorophore but not the acceptor fluorophore, so that a signal emitted by the donor fluorophore specifically excites the acceptor fluorophore as each nucleotide is added to the synthesized complementary strand by the polymerase. The electromagnetic radiation source is optional if LRET is used. A decoding means then converts a series of characteristic signals emitted by the acceptor fluorophores into a nucleic acid sequence that corresponds to the nucleic acid sequence of the complement.

In particular embodiments, the substrate may be a glass microscope slide or a three-dimensional matrix. In addition, the electromagnetic radiation is from a laser that emits light of the particular wavelength, and the viewing means includes a microscope objective. The detection means of the device may include a CCD camera, and the decoding means (which converts the series of unique signals into a nucleic acid sequence) is a digital computer.

In yet another embodiment, the device for sequencing a nucleic acid is a glass microscope slide to which an oligonucleotide primer, sample nucleic acid, or polymerase is attached, and the polymerase includes a GFP donor fluorophore. A laser is positioned to stimulate the donor fluorophore at a specific wavelength, and the donor fluorophore emits a first signal that induces the acceptor fluorophore to emit a signal when the acceptor fluorophore is brought sufficiently close to the donor fluorophore during chain elongation. The signal emitted by the acceptor fluorophore is unique to each type of nucleotide (e.g. A, T/U, C or G), so that the emitted signal indicates the nucleotide that is added to the complement. A microscope objective is positioned to view the sequence of signals emitted by the individual acceptor fluorophore molecules as the nucleotides are added to the polymerase. A spectrophotometer then converts the sequence of signals into a series of spectrographic signals that correspond to the series of signals emitted by the acceptor fluorophore. A CCD camera detects the sequence of signals and a digital computer converts the sequence of signals into a nucleic acid sequence.

The foregoing and other objects, features, and advantages of the disclosed method will become more apparent from the following detailed description of several embodiments which proceeds with reference to the accompanying figures.

DETAILED DESCRIPTION OF SEVERAL EMBODIMENTS

Abbreviations and Definitions

The following definitions and methods are provided to better define the materials and methods disclosed herein, and to guide those of ordinary skill in the art and in the practice of the materials and methods disclosed herein. As used herein (including the appended claims), the singular forms "a" or "an" or "the" include plural referents unless the context clearly dictates otherwise. Thus, for example, reference to "a protein" includes a plurality of such proteins and reference to "the affinity tag" includes reference to one or more affinity tags and equivalents thereof known to those skilled in the art, and so forth.

RT: Room temperature

Acceptor fluorophore: Acceptor fluorophores will generally be compounds which absorb energy from the donor fluorophore in the range of about 400 to 900 nm, usually in the range of about 500 to 800 nm. Acceptor fluorophores in the disclosed embodiments have an excitation spectra which overlaps with the emission of the donor fluorophore, such that energy emitted by the donor can excite the acceptor. The acceptor fluorophores are capable of being attached to nucleotides.

Acceptor fluorophores will generally absorb light at a wavelength which is usually at least 10 nm higher, more usually at least 20 nm higher, than the maximum absorbance wavelength of the donor fluorophore, and will have a fluorescence emission maximum at a wavelength ranging from about 400 to 900 nm. Acceptor fluorophores may be rhodamines, fluorescein derivatives, Green Fluorescent Protein (GFP), BODIPY® dye (4,4-difluoro-4-bora-3a,4a-diaza-s-indacene) and cyanine dyes. Specific acceptor fluorescer moieties include 5-carboxyfluorescein (FAM), 2'7'-dimethoxy-4'5'-dichloro-6-carboxyfluorescein (JOE), N,N,N',N'-tetramethyl-6-carboxyrhodamine (TAMRA), 6-carboxy-X-rhodamine (ROX), BODIPY® dye and cyanine dyes. Additional fluorophores which may be used in the herein disclosed method are listed below.

Affinity Tag: A molecule, such as a protein, attached to the N- or C-terminus of a recombinant protein using genetic engineering methods, to aid in the purification of the recombinant protein. Examples of affinity tags include, but are not limited to: histidine, S-tag, glutathione-S-transferase (GST) and streptavidin. Affinity tags may also be used to attach a protein or nucleic acid to a substrate.

cDNA (complementary DNA): A piece of DNA lacking internal, non-coding segments (introns) and regulatory sequences which determine transcription. cDNA can be synthesized in the laboratory by reverse transcription from messenger RNA extracted from cells.

Characteristic Signal: The resulting signal emitted from a fluorescently-labeled nucleotide, which can be predicted by the fluorophore(s) attached to the nucleotide.

Complementary: As referred to herein, nucleic acids that are "complementary" can be perfectly or imperfectly complementary, as long as the desired property resulting from the complementarity is not lost, e.g., ability to hybridize.

Donor Fluorophore: The donor fluorophore will generally be compounds which absorb in the range of about 300 to 900 nm, usually in the range of about 350 to 800 nm, and are capable of transferring energy to the acceptor fluorophore. The donor fluorophore will have a strong molar absorbance co-efficient at the desired excitation wavelength, for example greater than about $10^3$ $M^{-1}$ $cm^{-1}$. A variety of compounds may be employed as donor fluorescer components, including fluorescein, GFP, phycoerythrin, BODIPY® dye, DAPI (4', 6-diamidino-2-phenylindole), Indo-1, coumarin, dansyl, and cyanine dyes. Specific donor labels of interest include fluorescein, rhodamine, and cyanine dyes. Other fluorophores that can be used in the method disclosed herein are provided below.

In other embodiments, the donor fluorophore is a luminescent molecule, such as aequorin, as discussed below.

Electromagnetic Radiation: A series of electromagnetic waves that are propagated by simultaneous periodic variations of electric and magnetic field intensity, and that includes radio waves, infrared, visible light, ultraviolet light, X-rays and gamma rays. In particular embodiments, electromagnetic radiation can be emitted by a laser, which can possess properties of monochromaticity, directionality, coherence, polarization, and intensity. Lasers are particularly useful sources of electromagnetic energy for the method disclosed herein, because lasers are capable of emitting light at a particular wavelength (or across a relatively narrow range of wavelengths), such that energy from the laser can excite a donor but not an acceptor fluorophore.

Emission Signal The wavelength of light generated from a fluorophore after the fluorophore absorbs an excitation wavelength of light.

Emission Spectrum: The broad energy spectra which results after a fluorophore is excited by a specific wavelength of light. Each fluorophore has its own unique emission spectrum. Therefore, when individual fluorophores are attached to nucleotides, the emission spectrums from the fluorophores provide a means for distinguishing between the different nucleotides.

Excitation Signal: The wavelength of light necessary to raise a fluorophore to a state such that the fluorophore will emit a longer wavelength of light.

Fluorophore: A chemical compound, which when excited by exposure to a particular wavelength of light, emits light (i.e., fluoresces), for example at a different wavelength.

Also encompassed by the term "fluorophore" are luminescent molecules, which are chemical compounds which do not require exposure to a particular wavelength of light to fluoresce; luminescent compounds naturally fluoresce. Therefore, the use of luminescent signals eliminates the need for an external source of electromagnetic radiation, such as a laser. An example of a luminescent molecule includes, but is not limited to, aequorin (Tsien, 1998, *Ann. Rev. Biochem.* 67:509). Further description is provided below.

Examples of fluorophores that may be used in the method disclosed herein are provided in U.S. Pat. No. 5,866,366 to Nazarenko et al.: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), LISSAMINE™ rhodamine B sulfonyl chloride dye, rhodamine (Rhod), rhodamine B, rhodamine 123, rhodamine X isothiocyanate, sulforhodamine B, sulforhodamine 101 and sulfonyl chloride derivative of sulforhodamine 101 (TEXAS RED® dye); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999).

Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al., herein incorporated by reference) and derivatives thereof. Other fluorophores known to those skilled in the art may also be used, for example those available from Molecular Probes (Eugene, Oreg.).

The fluorophores disclosed herein may be used as a donor fluorophore or as an acceptor fluorophore. Particularly useful fluorophores have the ability to be attached to a polymerase or a nucleotide, are stable against photobleaching, and have high quantum efficiency. In addition, the fluorophores on different sets of nucleotides (e.g. A, T/U, G, C) are advantageously selected to have distinguishable emission spectra, such that emission from one fluorophore (such as A) is distinguishable from the fluorophore carried by another nucleotide (such as T).

Fluorescence resonance energy transfer (FRET): A process in which an excited fluorophore (the donor) transfers its excited state energy to a light absorbing molecule (the acceptor). This energy transfer is non-radioactive, and due primarily to a dipole-dipole interaction between the donor and acceptor fluorophores. This energy can be passed over a distance, for example a limited distance such as 10-100 Å. Limitation on the distance over which the energy can travel helps limit transfer to a desired target (such as between a donor fluorophore on a polymerase and a target acceptor fluorophore on a nucleotide, without collateral stimulation of other acceptor fluorophores).

FRET pairs: Sets of fluorophores that can engage in fluorescence resonance energy transfer (FRET). Examples of FRET pairs that can be used are listed below. However, one skilled in the art will recognize that numerous other combinations of fluorophores can be used.

FAM is most efficiently excited by light with a wavelength of 488 nm, emits light with a spectrum of 500 to 650 nm, and has an emission maximum of 525 nm. FAM is a suitable donor fluorophore for use with JOE, TAMRA, and ROX (all of which have their excitation maximum at 514 nm, and will not be significantly stimulated by the light that stimulates FAM).

The GFP mutant H9-40 (Tsien, 1998, *Ann. Rev. Biochem.* 67:509), which is excited at 399 nm and emits at 511 nm, may serve as a suitable donor fluorophore for use with BODIPY® dye, fluorescein, RHODAMINE GREEN™ dye and OREGON GREEN® dye. In addition, the fluorophores tetramethylrhodamine, LISSAMINE™, TEXAS RED® dye and naphthofluorescein can be used as acceptor fluorophores with this GFP mutant.

The fluorophore 3-($\epsilon$-carboxy-pentyl)-3'-ethyl-5,5'-dimethyloxacarbocyanine (CYA) is maximally excited at 488 nm and may therefore serve as a donor fluorophore for fluorescein or rhodamine derivatives (such as R6G, TAMRA, and ROX) which can be used as acceptor fluorophores (see Hung et al., *Analytical Biochemistry,* 243:15-27, 1996). However, CYA and FAM are not examples of a good FRET pair, because both are excited maximally at the same wavelength (488 nm).

One of ordinary skill in the art can easily determine, using art-known techniques of spectrophotometry, which fluorophores will make suitable donor-acceptor FRET pairs.

Fusion Protein: A protein comprising two amino acid sequences that are not found joined together in nature. The term "GFP-polymerase fusion protein" refers to a protein that includes a first amino acid sequence and a second amino acid sequence, wherein the first amino acid sequence is a GFP molecule (mutant or wild-type) and the second amino acid sequence is a polymerase. The link between the first and second domains of the fusion protein is typically, but not necessarily, a peptide linkage. Similarly, the term "GFP-aequorin fusion protein" refers to a protein that includes a first amino acid sequence and a second amino acid sequence, wherein the first amino acid sequence is a GFP molecule (mutant or wild-type) and the second amino acid sequence is an aequorin. GFP-aequorin fusion proteins can be generated using the method of Baubet et al. (*Proc. Natl. Acad. Sci. USA* 97:7260-5, 2000, herein incorporated by reference).

These fusion proteins may also be represented by the formula X-Y wherein X is a fluorophore, such as GFP, and Y is a polymerase protein. In a further embodiment of the fusion proteins disclosed, an affinity tag sequence may be linked to the N- or C-terminus of the first protein. Such a three part protein can thus be represented as T-X-Y wherein T is the affinity tag, X is a protein, such as a fluorescent protein and Y is a polymerase protein.

Green fluorescent protein (GFP): The source of fluorescent light emission in *Aequorea victoria*. As used herein, GFP refers to both the wild-type protein, and spectrally shifted mutants thereof, for example as described in Tsien, 1998, *Ann. Rev. Biochem.* 67:509 and in U.S. Pat. Nos. 5,777,079 and 5,625,048 to Tsien and Heim, herein incorporated by reference. In particular embodiments, GFP is excited using a laser. In other embodiments, GFP is excited using aequorin, for example using a GFP-aequorin fusion protein.

GFP-polymerase: Recombinant fusion protein containing both a functional GFP molecule and a functional polymerase. The GFP can be located at the N- or C-terminus of the polymerase. Alternatively, the GFP molecule can be located anywhere within the polymerase. Regardless of GFP position, it is important that the polymerase remain functional (i.e. able to catalyze the elongation of the complementary nucleic acid strand). The GFP-polymerase may also contain an affinity tag to aid in its purification and/or attachment to a substrate (Tag-GFP-polymerase). Furthermore, the GFP-polymerase may also contain a functional aequorin sequence, for example if the use of LRET is desired.

Linker: Means by which to attach a polymerase or a nucleic acid to a substrate. The linker ideally does not significantly interfere with binding to or incorporation by the polymerase. The linker can be a covalent or non-covalent means of attachment. In one embodiment, the linker is a pair of molecules, having high affinity for one another, one molecule on the polymerase (such as an affinity tag), the other on the substrate. Such high-affinity molecules include streptavidin and biotin, histidine and nickel (Ni), and GST and glutathione. When the polymerase and substrate are brought into contact, they bind to one another due to the interaction of the high-affinity molecules.

In another embodiment, the linker is a straight-chain or branched amino- or mercapto-hydrocarbon with more than two carbon atoms in the unbranched chain. Examples include aminoalkyl, aminoalkenyl and aminoalkynyl groups. Alternatively, the linker is an alkyl chain of 10-20 carbons in length, and may be attached through a Si—C direct bond or through an ester, Si—O—C, linkage (see U.S. Pat. No. 5,661,028 to Foote, herein incorporated by reference). Other linkers are provided in U.S. Pat. No. 5,306,518 to Prober et al., column 19; and U.S. Pat. No. 4,711,955 to Ward et al., columns 8-9; and U.S. Pat. No. 5,707,804 to Mathies et al., columns 6-7 (all herein incorporated by reference).

Several methods for attaching nucleic acids to a substrate are available. For example, methods for attaching the oligonucleotide primer to the substrate via a linker are disclosed in U.S. Pat. No. 5,302,509 to Cheeseman, herein incorporated by reference. Other methods for attaching a nucleic acid (for example the oligonucleotide primer or the nucleic acid to be sequenced) to the substrate include, but are not limited to: synthesizing a 5' biotinylated nucleic acid and affixing it to a streptavidin coated substrate (Beaucage, *Tetrahedron Letters* 22:1859-62, 1981; Caruthers, *Meth. Enzym.* 154:287-313, 1987), (Hultman, *Nucl. Acids Res.* 17:4937-46, 1989); drying the nucleic acid on amino-propyl-silanized (APS) glass (Ha et al. *Proc. Natl. Acad. Sci. USA.* 93:6264-68, 1996); and cross-linking the nucleic acid to an unmodified substrate by conjugating an active silyl moiety onto a nucleic acid (Kumar et al. *Nucleic Acids Res.* 28:e71, 2000).

Luminescence Resonance Energy Transfer (LRET): A process similar to FRET, except that the donor molecule is itself a luminescent molecule, or is excited by a luminescent molecule, instead of a laser. The luminescent molecule is naturally in an excited state; it does not require excitation by an external source of electromagnetic radiation, such as a laser. This will decrease the background fluorescence. In particular embodiments, the luminescent molecule can be attached to a polymerase, for example GFP-polymerase, as a means to produce local excitation of the GFP donor fluorophore, without the need for an external source of electromagnetic radiation. In other embodiments, the luminescent molecule is the donor fluorophore. In this embodiment, the fluorescence emitted from the luminescent molecule excites the acceptor fluorophores.

An example of luminescent molecule that can be used includes, but is not limited to, aequorin. The bioluminescence from aequorin, which peaks at 470 nm, can be used to excite a donor GFP fluorophore (Tsien, 1998, *Ann. Rev. Biochem.* 67:509; Baubet et al., 2000, *Proc. Natl. Acad. Sci. U.S.A.,* 97:7260-5). GFP transfers its resonance to the acceptor fluorophores disclosed herein. In this example, both aequorin and GFP can be attached to the polymerase.

Nucleic Acid: As used herein, nucleic acid refers to both DNA and RNA molecules. A sample nucleic acid molecule is a nucleic acid to be sequenced, and can be obtained in purified form, by any method known to those skilled in the art. For example, as described in U.S. Pat. No. 5,674,743 to Ulmer, herein incorporated by reference.

Nucleotides: The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). The nucleotides disclosed herein also include nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Such modifications however, allow for incorporation of the nucleotide into a growing nucleic acid chain. That is, they do not result in the termination of nucleic acid synthesis.

The choice of nucleotide precursors is dependent on the nucleic acid to be sequenced. If the template is a single-stranded DNA molecule, deoxyribonucleotide precursors (dNTPs) are used in the presence of a DNA-directed DNA polymerase. Alternatively, ribonucleotide precursors (NTPs) are used in the presence of a DNA-directed RNA polymerase. However, if the nucleic acid to be sequenced is RNA, then dNTPs and an RNA-directed DNA polymerase are used.

A "type" of nucleotide refers to a set of nucleotides that share a common characteristic that is to be detected. For example, the types of nucleotides may be divided into four types: A, T, C and G (for DNA) or A, U, C and G (for RNA). In this example, each type of nucleotide of the method disclosed herein will be labeled with a unique acceptor fluorophore, so as to be distinguishable from the other types by fluorescent spectroscopy or by other optical means. Such fluorophores are known in the art and include those listed above. The fluorescent label generally is not part of the 3'-OH group, so as to allow the polymerase to continue to add subsequent nucleotides.

Oligonucleotide: A polynucleotide is a linear sequence of up to about 200 nucleotide bases in length, for example a polynucleotide (such as DNA or RNA) which is at least 6 nucleotides, for example at least 15, 50, 100 or even 200 nucleotides long.

ORF (open reading frame): A series of nucleotide triplets (codons) coding for amino acids without any termination codons. These sequences are usually translatable into a peptide.

Polymerase: The enzyme which catalyzes the elongation of the primer strand, in the 5' to 3' direction along the nucleic acid template to be sequenced. Examples of polymerases which may be used in the method disclosed herein include, but are not limited to: the E. coli DNA polymerase I, specifically the Klenow fragment which has 3' to 5' exonuclease activity, Taq polymerase, reverse transcriptase, E. coli RNA polymerase, and wheat germ RNA polymerase II.

The choice of polymerase is dependent on the nucleic acid to be sequenced. If the template is a single-stranded DNA molecule, a DNA-directed DNA or RNA polymerase may be used; if the template is a single-stranded RNA molecule, then a reverse transcriptase (i.e., an RNA-directed DNA polymerase) may be used.

Polynucleotide: A linear nucleic acid sequence of any length. Therefore, a polynucleotide includes molecules which are 15, 50, 100, 200 (oligonucleotides) and also nucleotides as long as a full length cDNA.

Primer: Short nucleic acids, for example DNA oligonucleotides 10 nucleotides or more in length, which are annealed to a complementary target nucleic acid strand by nucleic acid hybridization to form a hybrid between the primer and the target nucleic acid strand, then extended along the target nucleic acid strand by a polymerase enzyme. Therefore, individual primers can be used for nucleic acid sequencing. In addition, primer pairs can be used for amplification of a nucleic acid sequence, e.g., by the polymerase chain reaction (PCR) or other nucleic-acid amplification methods known in the art.

Primers comprise at least 10 nucleotides of the nucleic acid sequences to be sequenced. In order to enhance specificity, longer primers may also be employed, such as primers having 15, 20, 30, 40, 50, 60, 70, 80, 90 or 100 consecutive nucleotides of the nucleic acid sequences to be sequenced. Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences.

If the nucleic acid to be sequenced is DNA, the primer used may be DNA, RNA, or a mixture of both. If the nucleic acid to be sequenced is RNA, the primer used may be RNA or DNA.

Purified: The term purified does not imply absolute purity; rather, it is intended as a relative term. Thus, for example, a purified GFP-polymerase protein preparation is one in which the GFP-polymerase protein is more pure than the protein in its environment within a cell. Preferably, a preparation of a GFP-polymerase protein is purified such that the GFP-polymerase protein represents at least 50% of the total protein content of the preparation, but may be, for example 90 or even 98% of the total protein content.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Reverse Transcriptase: A template-directed DNA polymerase that generally uses RNA as its template.

RNA polymerase: Catalyzes the polymerization of activated ribonucleotide precursors that are complementary to the DNA template.

Sequence of signals: The sequential series of emission signals, including light or spectra signals, that are emitted from fluorescently labeled nucleotides as they are added to the growing complementary nucleic acid strand.

Substrate: Material in the microscope field of view that the polymerase or nucleic acid is attached to. In particular embodiments, the substrate is made of biocompatible material that is transparent to light, including glass and quartz. For example, the substrate may be a 3 cm long by 1 cm wide by 0.25 cm thick glass microscope slide. In another embodiment, the substrate can be a gel matrix, to allow sequencing in three-dimensions. In yet another embodiment, for example when LRET is used, the substrate can be opaque.

The substrate can be treated before use. For example, glass microscope slides can be washed by ultrasonication in water for 30 minutes, soaked in 10% NaOH for 30 minutes, rinsed with distilled water and dried in an 80° C. oven for 10 minutes or air-dried overnight.

Two dye sequencing (TDS): A method of sequencing nucleic acids using at least two sets of fluorophores, with one set on the nucleotides (a different acceptor dye for each class of nucleotides), and the other set on the polymerase (a donor dye). In particular embodiments, two sets of fluorophores are used.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Unique Emission Signal: The emission spectrum for each fluorophore is unique. By attaching one or more individual fluorophores or other labels to each type of nucleotide, each different type of nucleotide (e.g. A, T/U, C or G) has its own individual or own combination of signals (such as fluorophores that emit at unique different wavelengths). Each nucleotide class will have a unique emission signal, that in the examples is based on the fluorophore(s) present on that class of nucleotide. This signal can be used to determine which type of nucleotide (e.g. A, T/U, C or G) has been added to a growing complementary strand of nucleic acid, and these signals in combination indicate the nucleic acid sequence.

In addition to the different wavelengths of light emitted as a signal, different types of signals can include different intensities of light and different intensities emitted at a particular wavelength. In other words, a spectrum consisting of different intensities emitted at different wavelengths.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Detailed Embodiment

Figure 1A:
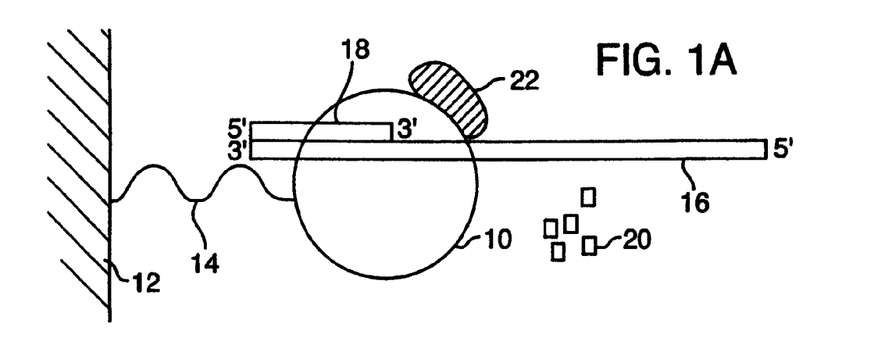
FIG. 1A is a schematic drawing showing the attachment of a polymerase to a substrate, and the polymerase associated with a template and primer strand.
Figure 2:
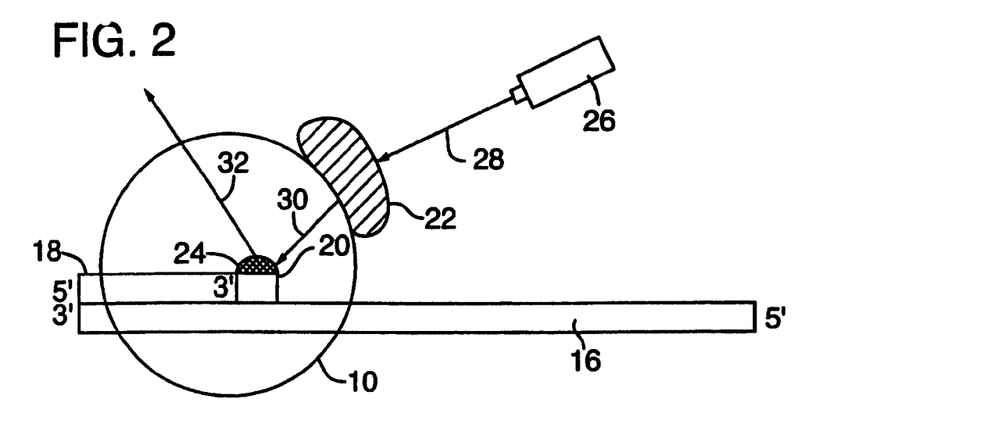
FIG. 2 is a schematic drawing illustrating fluorescence resonance energy transfer (FRET) between a donor fluorophore on a polymerase and an acceptor fluorophore on a nucleotide. Note that a laser 26 which emits electromagnetic radiation 28 is not required for luminescence resonance energy transfer (LRET).
Figure 3:
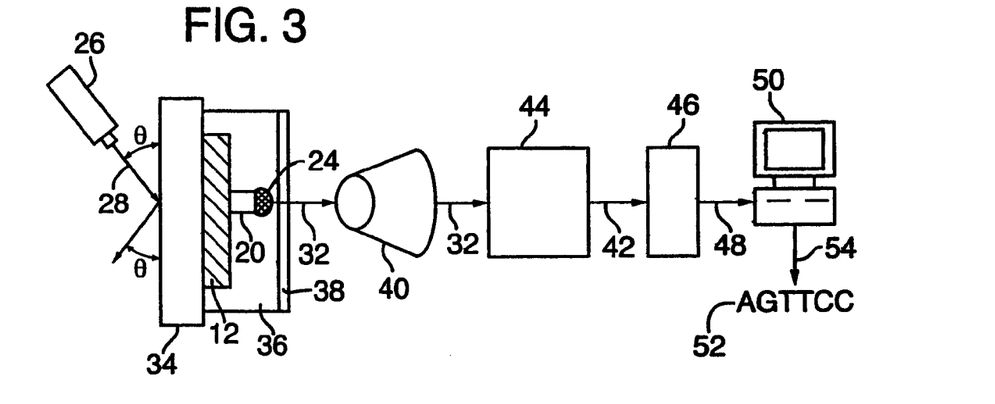
FIG. 3 is a schematic drawing illustrating a microscope and computer assembly that can be used to sequence nucleic acids using TDS. Note that a laser 26 which emits electromagnetic radiation 28 is not required for LRET.

Disclosed herein is a new method for sequencing nucleic acids, and one disclosed embodiment is called Two Dye Sequencing (TDS), because it depends on at least two classes of fluorophores, a donor and an acceptor. The donor fluorophore is on a polymerase, and the acceptor fluorophore is on the nucleotides which are incorporated into the nucleic acid as a complementary strand is generated (FIGS. 1-3). In one embodiment, as shown in FIG. 1A, a polymerase 10, is attached to a substrate 12, such as a microscope slide, by a linker 14. The nucleic acid 16 to be sequenced has an annealed oligonucleotide primer 18, and is bound by the anchored polymerase 10. To start the sequencing reaction, a mixture of nucleotides 20 is added. The polymerase 10 then sequentially adds the appropriate nucleotide 20 to the complementary strand. As shown in FIG. 3, the substrate 12, can be mounted onto a microscope stage 34. The sequencing reaction may take place in an aqueous environment 36, which may be sealed to prevent desiccation, for example by covering with a glass cover slip 38.

Figure 1B:
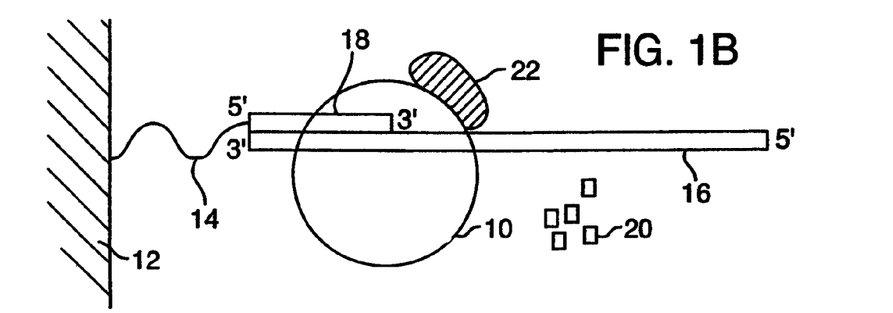
FIG. 1B is a schematic drawing showing the attachment of an oligonucleotide primer to a substrate, and the polymerase associated with a template and primer strand.
Figure 1C:
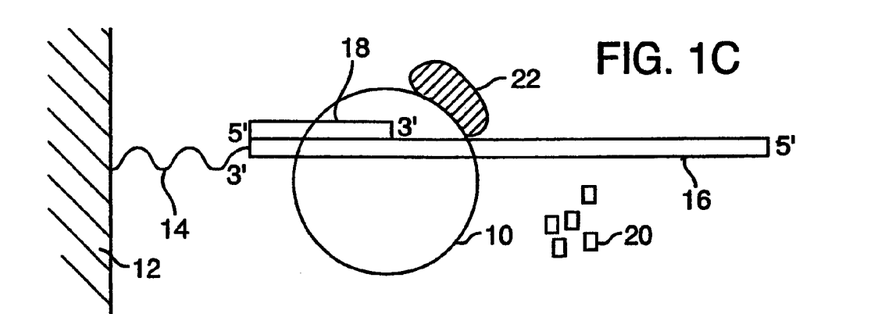
FIG. 1C is a schematic drawing showing the attachment of a nucleic acid to be sequenced by its 3' end, a substrate, and the polymerase associated with a template and primer strand.
Figure 1D:
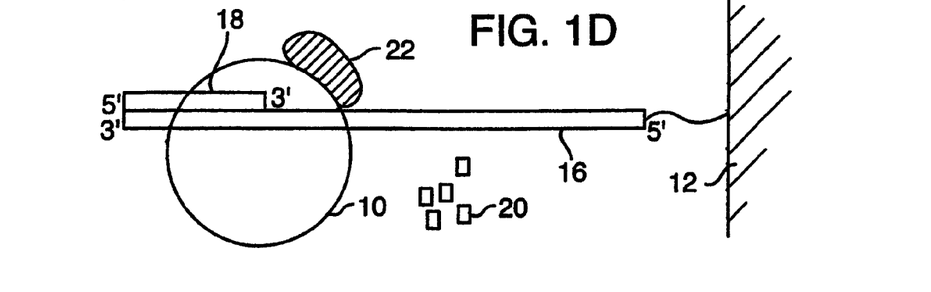
FIG. 1D is a schematic drawing showing the attachment of a nucleic acid to be sequenced by its 5' end, a substrate, and the polymerase associated with a template and primer strand.

FIGS. 1B-1D show alternative embodiments in which a nucleic acid, for example an oligonucleotide primer 18 (FIG. 1B) or a nucleic acid to be sequenced 16 (FIGS. 1C and 1D) is attached to a substrate 12, such as a microscope slide, by a linker 14. The nucleic acid to be sequenced can be attached by its 5' (FIG. 1D) or 3' end (FIG. 1C). In other embodiments, the nucleic acid to be sequenced can be attached to the substrate by any nucleotide within the nucleic acid. To start the sequencing reaction, a mixture of nucleotides 20 and polymerase 10 is added as described above.

FIG. 2 illustrates the fluorophores on both the polymerase 10 and the nucleotides 20. The polymerase 10 is labeled with a donor fluorophore 22, such as green fluorescent protein (GFP). The nucleotide 20 (A, T/U, C, or G) is labeled with at least one acceptor fluorophore 24. After attaching the fluorescent polymerase 10 to a substrate 12 in a microscope field of view, the fluorescent nucleotides 20 are added to the reaction chamber. While each nucleotide 20 is added to the complementary strand, the fluorophore 22 on the polymerase 10, but not the fluorophore(s) 24 on the nucleotides 20, is continually excited using electromagnetic radiation, for example a coherent beam of light provided by a laser 26 which emits electromagnetic radiation 28 of a particular wavelength, or light within a narrow range of wavelengths. Alternatively, the donor fluorophore 22 can be a luminescent molecule, or a luminescent molecule can be used to excite the donor fluorophore 22. In these embodiments, a source of electromagnetic radiation, such as a laser 26, is not required. An example of a luminescent molecule is aequorin.

The laser 26 provides an excitation signal 28 that excites the donor fluorophore 22 on the polymerase 10, but not the acceptor fluorophore 24 on the incorporated or free nucleotides 20. Upon addition of a fluorescent nucleotide 20 to the complementary strand, the emission signal 30 from the donor fluorophore 22 will excite the acceptor fluorophore 24 associated with the particular nucleotide being added to the sequence. The acceptor fluorophore 24 then emits its own unique emission signal 32, which acts as an indicator of the corresponding type of nucleotide (uniquely associated with that fluorophore) that has been added to the sequence. This transfer of energy from the donor fluorophore to the acceptor fluorophore is fluorescence resonance energy transfer (FRET). Alternatively, if a luminescent molecule such as aequorin (instead of a laser 26) is used to excite the donor fluorophore (or is the donor fluorophore), the resulting emission signal 30 from the donor fluorophore 22 (or luminescent molecule) will excite the acceptor fluorophore 24 associated with the particular nucleotide being added to the sequence, without the need for a source of electromagnetic radiation 26. The acceptor fluorophore 24 then emits its own unique emission signal 32, which acts as an indicator of the corresponding type of nucleotide (uniquely associated with that fluorophore) that has been added to the sequence. This transfer of energy is luminescent resonance energy transfer (LRET).

The unique emission signal 32 for each type of nucleotide 20 (A, T/U, C or G) is converted into a nucleic acid sequence as shown in FIG. 3. The series of emission signals 32, emitted in the microscope field as each nucleotide is added to the sequence, is collected with a microscope objective lens 40, and a complete emission spectrum 42 for each nucleotide emission 32 is generated by a spectrophotometer 44. The complete emission spectrum 42 is captured by a detection device, such as CCD-camera 46 for each nucleotide 20 as it is added to the nucleic acid strand 16 in the microscope field of view. The CCD camera 46 collects the emission spectrum 42 for each added nucleotide, and converts the spectrum 42 into a charge 48. The charge 48 for each nucleotide addition may be recorded by a computer 50, for converting the sequence of emission spectrums into a nucleic acid sequence 52 for each nucleic acid in the microscope field of view using an algorithm 54, such as a least-squares fit between the signal spectrum 42 and the dye spectra for the fluorophore 24 on each class of nucleotides 20.

Although many different algorithms could be used to convert the emission spectrums into a nucleic acid sequence, this specific example illustrates one approach. Four fluorescent spectra (Anm, Cnm, Gnm and T/Unm) are generated from macroscopic measurements. From the sample, an unknown noisy spectrum (Snm) is generated. The unknown spectrum is assumed to be the sum of the four known spectra with only four weights, a, c, g and t/u, representing the relative proportions of the bases. So at 520 nm through 523 nm, this results in five equations:

$$A520*a+C520*c+G520*g+T520*t=S520$$

$$A521*a+C521*c+G521*g+T521*t=S521$$

$$A522*a+C522*c+G522*g+T522*t=S522$$

$$A523*a+C523*c+G523*g+T523*t=S523$$

$$A524*a+C524*c+G524*g+T524*t=S524$$

Filling in the known values, a, c, g, and t/u are solved using a least squares linear regression.

In this particular example, the donor fluorophore 22 carried by the polymerase 10 is GFP H9-40, and the nucleotides are labeled with acceptor fluorophores as follows: A is labeled with BODIPY® dye; T is labeled with fluorescein; C is labeled with rhodamine; G is labeled with OREGON GREEN® dye. In another example, the donor fluorophore 22 carried by the polymerase 10 is H9-40, and the nucleotides are labeled with acceptor fluorophores as follows: A is labeled with tetramethylrhodamine; T/U is labeled with napthofluorescein; C is labeled with LISSAMINE™ dye; G is labeled with TEXAS RED® dye. The emission spectrum of each of the acceptor fluorophores is monitored, and the spectrum of each of the fluorophores can be distinguished from each other, so that the addition of each different type of nucleotide can be detected.

Therefore, the method allows for the sequencing of nucleic acids by monitoring the incorporation of individual nucleotides into individual DNA or RNA molecules on the molecular level, instead of sequencing by monitoring macromolecular events, such as a pattern on an electrophoresis gel, whose signal is representative of a large population of nucleic acid molecules. Using this method in combination with a large field of view, it is possible that 1000 or more DNA molecules could be sequenced simultaneously, at sequencing speeds of 360 bases or more per hour. Each DNA molecule to be copied/sequenced, and its associated polymerase/donor dye, may correspond to a particular field of view, or a particular sensor for a position in which the polymerase mediated reaction is occurring. Therefore, using multiple such devices, molecular sequencing with the method can permit sequencing entire chromosomes or genomes within a day.

More details about particular aspects of this method are given in the following examples.

Example 1

Preparation of Fluorescent or Luminescent Polymerases

This example describes how to prepare polymerases containing at least one fluorophore or luminescent molecule. The fluorophore or luminescent molecule may be a donor fluorophore.

Recombinant GFP-Polymerase

Green fluorescent protein (GFP) includes a chromophore formed by amino acids in the center of the GFP. GFP is photostable, making it a desirable fluorophore to use on the polymerase, because it is resistant to photobleaching during excitation. Wild-type GFP is excited at 393 nm or 476 nm to produce an emission at 508 nm.

GFP mutants have alternative excitation and emission spectra. One GFP mutant, H9-40 (Tsien, 1998, *Ann. Rev. Biochem.* 67:509; U.S. Pat. Nos. 5,625,048 and 5,777,079 to Tsien and Heim, herein incorporated by reference), has only a single absorption at 398 nm and emits at 511 nm. A red-shifted GFP mutant RSGFP4 (Delagrave et al., *Biotechnology* 13:151-4, 1995) has an excitation at 490 nm and emission at 505 nm. The blue-shifted GFP mutant BFP5 absorbs at 385 nm and emits at 450 nm (Mitra et al., *Gene,* 173:13-7, 1996).

The polymerase used for elongation of the primer strand can be attached to GFP to generate a fusion protein, GFP-polymerase, by recombinant techniques known to those skilled in the art. Methods for making fusion proteins are described in Sambrook et al. (*Molecular Cloning, A Laboratory Manual*, Cold Spring Harbor Laboratory, Cold Spring Harbor, N.Y., Chapter 17, 1989), herein incorporated by reference. Plasmids containing the wild-type or mutant GFP gene sequences and a multiple cloning site (MCS) into which the polymerase sequence can be inserted (i.e. pGFP), are available from Clontech (Palo Alto, Calif.).

Briefly, both the polymerase DNA and the GFP plasmid are digested with the appropriate restriction enzyme(s) which allow for the insertion of the polymerase into the MCS of the GFP plasmid in the sense orientation. The resulting fragments are ligated and expressed in bacteria, such as *E. coli*. The expressed recombinant GFP-polymerase is then purified using methods known by those skilled in the art. The GFP molecule may be placed at the N- or C-terminus of the polymerase, or anywhere in between. The resulting GFP-polymerases are tested to determine which has the optimal properties for sequencing. Such properties can include: ease of protein purification, amount of protein produced, amount of fluorescence signal emitted after excitation, minimal alteration of the fluorescent properties of the GFP.

The purification of recombinant fusion proteins has been made significantly easier by the use of affinity tags that can be genetically engineered at either the N- or C-terminus of recombinant proteins. Such tags can be attached to the GFP-polymerase protein, to aid in its purification and subsequent attachment to a substrate (see Example 2). Examples of affinity tags include histidine (His), streptavidin, S-tags, and glutathione-S-transferase (GST). Other tags known to those skilled in the art can also be used.

In general, the affinity tags are placed at the N- or C-terminus of a protein. Commercially available vectors contain one or multiple affinity tags. These vectors can be used directly, or if desired, the sequences encoding the tag can be amplified from the vectors using PCR, then ligated into a different vector such as the GFP-containing vectors described above. To prepare a Tag-GFP-polymerase recombinant fusion protein, vectors are constructed which contain sequences encoding the tag, GFP (wild-type or mutant), and the polymerase. The sequences are ordered to generate the desired Tag-GFP-polymerase recombinant fusion protein. Such methods are well known to those skilled in the art (Sambrook et al., *Molecular Cloning, A Laboratory Manual*, Cold Spring Harbor Laboratory, Cold Spring Harbor, N.Y., Chapter 17, 1989). This vector is expressed in bacteria such as *E. coli*, and the protein purified. The method of purification will depend on the affinity tag attached. Typically, the bacterial lysate is applied to a column containing a resin having high affinity for the tag on the fusion protein. After applying the lysate and allowing the tagged-fusion protein to bind, unbound proteins are washed away, and the fusion protein is subsequently eluted.

One of the most widely used tags is six or ten consecutive histidine (His) residues, which has high affinity for metal ions. A His-6 or His-10 moiety can be attached to GFP-polymerase by using pET vectors (Novagen, Madison, Wis.). The generation of GFP-His (Park and Raines, *Protein Sci.* 6:2344-9, 1997) and protein-GFP-His recombinant proteins have been described previously (Prescott et al., *FEBS Lett.* 411:97-101, 1997, herein incorporated by reference). The His-containing fusion proteins can be purified as described in Paborsky et al. (*Anal. Biochem.,* 234:60-5, 1996), herein incorporated by reference. Briefly, the cell lysate is immobilized using affinity chromatography on $Ni^{2+}$-NTA-Agarose (QIAGEN, Valencia, Calif.). After washing away unbound proteins, for example using a buffer containing 8 mM imidazole, 50 mM Tris HCl, pH 7.5, 150 mM NaCl, the bound recombinant protein is eluted using the same buffer containing a higher concentration of imidazole, for example 100-500 mM.

The S-tag system is based on the interaction of the 15 amino acid S-tag peptide with the S-protein derived from pancreatic ribonuclease A. Several vectors for generating S-tag fusion proteins, as well as kits for the purification of S-tagged proteins, are available from Novagen (Madison, Wis.). For example vectors pET29a-c and pET30a-c can be used. The S-tag fusion protein is purified by incubating the cell lysate with S-protein agarose, which retains S-tag fusion proteins. After washing away unbound proteins, the fusion protein is released by incubation of the agarose beads with site-specific protease, which leaves behind the S-tag peptide.

The affinity tag streptavidin binds with very high affinity to D-biotin. Vectors for generating streptavidin-fusion proteins, and methods for purifying these proteins, are described in Santo and Cantor (*Biochem. Biophys. Res. Commun.* 176: 571-7, 1991, herein incorporated by reference). To purify the fusion protein, the cell lysate is applied to a 2-iminobiotin agarose column, (other biotin-containing columns may be used), and after washing away unbound proteins, the fusion protein is eluted, for example with 6 M urea, 50 mM ammonium acetate (pH 4.0).

The enzyme glutathione-S-transferase (GST) has high affinity for glutathione. Plasmid expression vectors containing GST (pGEX) are disclosed in U.S. Pat. No. 5,654,176 to Smith, herein incorporated by reference and in Sharrocks (Gene, 138:105-8, 1994, herein incorporated by reference). pGEX vectors are available from Amersham Pharmacia Biotech (Piscataway, N.J.). The cell lysate is incubated with glutathione-agarose beads and after washing, the fusion protein is eluted, for example, with 50 mM Tris-HCl (pH 8.0) containing 5 mM reduced glutathione. After purification of the GST-GFP-polymerase fusion protein, the GST moiety can be released by specific proteolytic cleavage. If the GST-fusion protein is insoluble, it can be purified by affinity chromatography if the protein is solubilized in a solubilizing agent, which does not disrupt binding to glutathione-agarose, such as 1% Triton X-100, 1% Tween 20, 10 mM dithiothreitol or 0.03% NaDodSO$_4$. Other methods used to solubilize GST-fusion proteins are described by Frangioni and Neel (*Anal. Biochem.* 210:179-87, 1993, herein incorporated by reference).

Recombinant GFP-Aequorin-Polymerase

Recombinant GFP-aequorin-polymerase can be generated using methods known to those skilled in the art, for example the method disclosed by Baubet et al. (*Proc. Natl. Acad. Sci. USA* 97:7260-5, 2000, herein incorporated by reference).

Briefly, aequorin cDNA (for example Genbank Accession No. L29571), polymerase DNA, and a GFP plasmid are digested with the appropriate restriction enzyme(s) which allow for the insertion of the aequorin and polymerase into the MCS of a GFP plasmid in the sense orientation. The resulting fragments are ligated and expressed in bacteria, such as *E. coli*. The expressed recombinant GFP-aequorin-polymerase is then purified as described above. Affinity tags can also be added.

The ordering of the GFP, aequorin, and polymerase sequences can be optimized. The resulting GFP-aequorin-polymerases are tested to determine which has the optimal properties for sequencing. Such properties can include: ease of protein purification, amount of protein produced, amount of chemiluminescent signal emitted, amount of fluorescent signal emitted after excitation, minimal alteration of the fluorescent properties of the GFP and aequorin, and amount of polymerase activity Attachment of Fluorophores to a Polymerase As an alternative to generating a GFP-polymerase fusion protein, other donor fluorophores can be used by directly or indirectly attaching them to the polymerase.

Amine-reactive fluorophores are frequently used to create fluorescently-labeled proteins. Examples of amine-reactive probes that can be used include, but are not limited to: fluorescein, BODIPY® dye, rhodamine, TEXAS RED® dye and their derivatives. Such dyes will attach to lysine residues within the polymerase, as well as to the free amine at the N-terminus. Reaction of amine-reactive fluorophores usually proceeds at pH values in the range of pH 7-10.

Alternatively, thiol-reactive probes can be used to generate a fluorescently-labeled polymerase. In proteins, thiol groups are present in cysteine residues. Reaction of fluors with thiols usually proceeds rapidly at or below room temperature (RT) in the physiological pH range (pH 6.5-8.0) to yield chemically stable thioesters. Examples of thiol-reactive probes that can be used include, but are not limited to: fluorescein, BODIPY® dye, cumarin, rhodamine, TEXAS RED® dye and their derivatives.

Other functional groups on the protein including alcohols (serine, threonine, and tyrosine residues), carboxylic acids and glutamine, can be used to conjugate other fluorescent probes to the polymerase.

Another fluorophore which can be attached to the polymerase is 4-[N-[(iodoacetoxy)ethyl]-N-methylamino]-7-nitrobenz-2-oxa-1,3-diazole (IANBD), as described by Allen and Benkovic (*Biochemistry*, 1989, 28:9586).

Methods for labeling proteins with reactive dyes are well known to those well skilled in the art. In addition, the manufacturers of such fluorescent dyes, such as Molecular Probes (Eugene, Oreg.), provide instructions for carrying out such reactions.

In particular embodiments, fluorescently-labeled polymerases have a high fluorescence yield, and retain the critical features of the polymerase, primarily the ability to synthesize a complementary strand of a nucleic acid molecule. The polymerase may therefore have a less-than-maximal fluorescence yield to preserve the function of the polymerase.

Following conjugation of the fluorophore to the polymerase, unconjugated dye is removed, for example by gel filtration, dialysis or a combination of these methods.

Example 2

Attachment of the Polymerase or Nucleic Acid to a Substrate

This example describes methods that can be used to attach the fluorescent polymerase generated in Example 1, or a nucleic acid, to a substrate, such as a microscope slide or gel matrix. During the sequencing reaction, the sample nucleic acid to be sequenced, the oligonucleotide primer, or the polymerase, is attached to a substrate in the microscope field of view.

Attachment of Nucleic Acids

Several methods for attaching nucleic acids (for example the sample nucleic acid to be sequenced or an oligonucleotide primer) to a substrate are available. In particular embodiments, nucleic acids can be attached by their 5' or 3' end, or anywhere in between. For example, a 5' biotinylated primer can be synthesized (Beaucage, *Tetrahedron Letters* 22:1859-62, 1981; Caruthers, *Meth. Enzym.* 154:287-313, 1987), and affixed to a streptavidin coated substrate surface (Hultman, *Nucl. Acids Res.* 17:4937-46, 1989). In another embodiment, the nucleic acid can be dried on amino-propyl-silanized (APS) glass, as described by Ha et al. (*Proc. Natl. Acad. Sci. USA.* 93:6264-68, 1996), herein incorporated by reference.

In yet other embodiments, a silyl moiety can be attached to a nucleic acid, which can be used to attach the nucleic acid directly to a glass substrate, for example using the methods disclosed by Kumar et al. (*Nucleic Acids Res.* 28:e71, 2000, herein incorporated by reference). Briefly, silane is conjugated to a nucleic acid using the following method.

Mercaptosilane [(3-Mercaptopropyl)-trimethoxysilane] is diluted to 5 mM stock solution with a reaction buffer such as sodium acetate (30 mM, pH 4.3) or sodium citrate (30 mM, pH 4). For conjugation of 5'-thiol-labeled nucleotides with mercaptosilane, 1 nmol nucleotides are reacted with 5 nmol mercaptosilane in 20 µl of the same buffer for 10-120 min at RT. The reaction mixture is used directly or diluted with the reaction buffer to a desired concentration for immobilization on a substrate, such as a glass microscope slide. 5'-acrylic-labeled oligonucleotides are conjugated to mercaptosilane using an identical procedure.

The 5'-thiol-labeled nucleotides are conjugated with aminosilane [(3-aminopropyl)-trimethoxysilane] in dimethylsulfoxide (DMSO) in the presence of heterobifunctional linkers N-succinimidyl-3-(2-pyridyldithiol)-propionate (SPDP) or succinimidyl-6-(iodoacetyl-amino)-hexanoate (SIAX). Nucleotides (final concentration 5-50 µM) are combined with 2.5 nmol aminosilane (added from 5 mM solution in ethanol) and 2.5 nmol bifunctional reagents (added from 5 mM stock solution in DMSO) in 10 µl DMSO, and the reaction allowed to proceed for 1-2 hours at RT.

Acrylic-labeled oligonucleotides (50-500 pmol) are combined with 25 nmol acrylicsilane (γ-methacryloxy-propyl-trimethoxysilane) in 10 µl of 30 mM NaOAc, pH 4.3. Ammonium persulfate (10% in H2O) and N,N,N',N'-tetramethylethylenediamine (TEMED) are added to final concentration of 0.5 and 2%, respectively, and the mixture allowed to react for 30 minutes at RT.

After the conjugation reactions, the reaction mixture is referred to as silanized nucleic acid, and can be directly used for spotting onto a substrate. Silanized nucleic acids can be spotted on the glass slides manually (120 nl/spot) or with an automated arrayer (Genetic Microsystem, Woburn. USA) (1 nl/spot). Nucleic acids in aqueous solutions can be kept in a humidified chamber for 15 minutes at RT after spotting onto the glass slide, dried at 50° C. for five minutes, dipped into boiling water for 30 seconds to remove non-covalently bound nucleic acids, and dried with nitrogen before hybridization. Nucleotides in DMSO are left at RT for 15 minutes after spotting onto glass slides and dried at 50° C. for 10 minutes. These slides are sequentially washed with DMSO (3×2 min), ethanol (3×2 min) and boiling water (2 min) and dried with nitrogen for later use.

To hybridize a complementary nucleotide to the nucleotide attached to the substrate, such as an oligonucleotide primer, the nucleotide to be hybridized is diluted to between 20 nM and 1 µM in 5×SSC (750 mM NaCl, 125 mM sodium citrate, pH 7) with 0.1% Tween-20. Hybridization is done under coverslips in a humidifier at 37° C. for 30 minutes to overnight. Non-hybridized and non-specific nucleotides are removed by washing with 5×SSC containing 0.1% Tween-20 (3×1 min) followed by 1×SSC containing 0.1% Tween-20 (2×15 min).

If a longer nucleic acid molecule is to be hybridized, such as a sample nucleic acid, hybridization is carried out at 65° C. for four hours in 3×SSC with 0.1% SDS and 1 µg/µl yeast tRNA. The slides are then washed with 1×SSC containing 0.1% SDS (3×2 min) and 0.1×SSC containing 0.1% SDS (3×5 min) at RT.

After washing, the slides can be dried with nitrogen gas. If repeated hybridization on the same substrate is desired, the substrate is boiled in water for one minute then dried with nitrogen gas before proceeding to the next hybridization reaction.

To attach a nucleic acid by the 3' end, a terminal transferase can be used to "tail" the molecule.

Attachment of Polymerase

In other embodiments the polymerase can be attached to the substrate. The polymerase can be linked to a substrate by first generating a streptavidin-polymerase fusion protein using the methods described above in Example 1. The polymerase-streptavidin protein is then affixed to a biotinylated substrate, for example as described by Mazzola and Fodor (*Biophys. J.* 68:1653-60, 1995) or Itakura et al. (*Biochem. Biophys. Res. Commun.* 196:1504-10, 1993).

Other methods of attaching the polymerase to a substrate are well known to those skilled in the art. For example, the microscopic tip of an atomic force microscope may be used to chemically alter the surface of a substrate (Travis, *Science* 268:30-1, 1995). Alternatively, if the protein contains 6-10 consecutive histidine residues, it will bind to a nickel-coated substrate. For example, Paborsky et al. (*Anal. Biochem.* 234: 60-5, 1996, herein incorporated by reference) describe a method for attaching nickel to a plastic substrate. To charge microtiter polystyrene plates, 100 µl of N,N-bis[caroboxymethyl]lysine (BCML) is added (10 mM BCML in 0.1 M NaPO$_4$, pH 8) to each well and incubated overnight at RT. The plate is subsequently washed with 200 µl of 0.05% Tween, blocked (3% BSA in 50 mM Tris HCl, pH 7.5, 150 mM NaCl, 0.05% Tween) and washed with a series of buffers. First 50 mM Tris HCl, pH 7.5, 500 mM imidazole, 0.05% Tween; second, 0.05% Tween; third, 100 mM EDTA, pH 8.0 and last 0.05% Tween. The plate is next incubated with 10 mM NiSO$_4$ for 20 minutes at RT. The plate is finally washed with 0.05% Tween and then 50 mM Tris HCl, 500 mM NaCl, pH 7.5.

Random attachment of the fluorescent polymerase to a substrate should be sufficient at low polymerase concentrations. To allow for the tightest packing of sequencing signals in the field of view, the polymerases may be arranged on a two-dimensional substrate surface in an organized array. Polymerases may be spaced by micrometer distances as described by Müller et al. (*Science* 268:272-3, 1995, herein incorporated by reference). In addition, patterns of channels that are approximately 50 µm in width and approximately 10-20 µm in depth, can be formed in the substrate using standard photolithographic procedures followed by chemical wet etching as described in U.S. Pat. No. 5,661,028 to Foote (herein incorporated by reference). Much smaller channels can be generated using nanolithography techniques. Dense periodic arrays of holes or chambers 20 nm across are fabricated into a silicon nitride coated substrate by the method of Park et al. (*Science*, 276:1401-4, 1997, herein incorporated by reference). In each chamber, a single sequencing reaction would take place. The polymerase may also be attached to the substrate in an orderly array by micropipetting droplets containing the polymerase onto the surface of the substrate. The droplets are then covered, for example with a glass coverslip, to prevent evaporation.

Embedding Polymerase and Nucleic Acid in a Gel Matrix

As an alternative to attaching the polymerase or nucleic acid to a two-dimensional surface, the polymerase or nucleic acid may be embedded into a three-dimensional gel matrix. The polymerase or nucleic acid is added to the liquid matrix, which is allowed to solidify, trapping the polymerases or nucleic acids within it. Examples of this type of matrix include agarose and acrylamide, for example Ni$^{2+}$-NTA-Agarose (QIAGEN, Valencia, Calif.).

Example 3

Preparation of Fluorescent Nucleotides

This example describes how to prepare nucleotides containing at least one fluorophore, for example an acceptor fluorophore. In addition, this example lists sources of commercially available fluorescent nucleotides that can be used in the present disclosure. When choosing acceptor fluorophores, it is important that the frequency used to excite the donor fluorophore on the polymerase (Example 1) not overlap the excitation spectra of the acceptor fluorophores on the nucleotides. Each nucleotide should possess at least one acceptor fluorophore having an excitation spectrum which overlaps the emission spectrum of the donor fluorophore attached to the polymerase (Example 1), such that the emission from the donor fluorophore excites the acceptor fluorophore.

NEN Life Science Products (Boston, Mass.) offers all four deoxynucleotides and ribonucleotide analogs with fluorophores attached. There are several different fluorophores available including fluorescein, TEXAS RED® dye, tetramethylrhodamine, coumarin, napthofluorescein, cyanine-3, cyanine-5, and LISSAMINE™ dye. In addition, Molecular Probes (Eugene, Oreg.) sells deoxyuridinetriphosphate (dUTP) labeled with various fluorophores replacing the methyl group of thymine, synthesized by the method of U.S. Pat. No. 5,047,519. Because these nucleotides have 3' hydroxyls, they can be used directly for sequencing.

Alternatively, nucleotides containing other acceptor fluorophores can be prepared. The fluorophores are capable of being attached to the nucleotide, are stable against photobleaching, and have high quantum efficiency. In addition, each type of nucleotide (e.g. A, T/U, C and G) will have a unique fluorophore (or a unique combination of fluorophores) attached, such that each type of nucleotide will have a distinct emission signal (such as an emission spectrum) from the other types of nucleotides. Hence a deoxynucleotide A will give a different emission signal from a nucleotide T, G or C; a nucleotide T will give a different emission signal from a nucleotide A, G or C; a nucleotide C will give a different emission signal from a nucleotide A, T or G; and a nucleotide G will give a different emission signal from a nucleotide A, T, or C. In the case of RNA, U will be substituted for T in this example.

The fluorophore ideally does not interfere excessively with the degree or fidelity of nucleotide incorporation. After attaching the fluorophores, the nucleotide is still able to undergo polymerization, complementary base pairing, and retain a free 3' hydroxyl end.

The fluorophore can either be directly or indirectly attached to the nucleotide. When attaching the fluorophore directly to the nucleotide, the method described above for attaching fluorophores to polymerases can be used (Example 1). Alternatively, the fluorophore may be attached indirectly to the nucleotide by a linker molecule. For example, a streptavidin linkage may be used. The linker does not significantly interfere with binding to or incorporation by the polymerase. The use of a linker would make the nucleotide bulky, allowing less FRET to previous bases. This may make it easier to distinguish nucleotides as they are added to the complementary nucleic acid strand. Alternatively, the nucleotides can be cleaved from the DNA molecules after their incorporation, for example by attaching DNase to the end of the polymerase, producing free mono nucleotides that could not be reused. In addition, fluorescent molecules containing two attachment points can be used to orient the fluorophore on the polymerase (Corrie et al., 1999, *Nature* 400:425, herein incorporated by reference).

The linkage can be peptidase sensitive, allowing the fluorophore to be released after the emission signal is detected as a result of the acceptor fluorophore on the nucleotide being added to the complementary nucleic acid strand. The use of a linker may allow the fluorophore orientation to be controlled, so that the optimal orientation for FRET can be determined. An optimal orientation is one that generates the brightest emission signal from the acceptor fluorophore, without the nucleotide losing its ability to incorporate into the complementary nucleic acid strand.

U.S. Pat. Nos. 5,047,519 and 5,151,507 to Hobbs et al. (herein incorporated by reference) teach the use of linkers to separate a nucleotide from a fluorophore. Examples of linkers may include a straight-chained alkylene, $C_1$-$C_{20}$, optionally containing within the chain double bonds, triple bonds, aryl groups or heteroatoms such as N, O or S. Substituents on the diradical moiety can include $C_1$-$C_6$ alkyl, aryl, ester, ether, amine, amide or chloro groups.

Unlike the 3' blocked methods of nucleic acid sequencing, the sequencing method described herein is asynchronous. Therefore, it can be difficult to distinguish multiple bases of the same type (i.e. poly T). To solve this problem, "dummy" nucleotides can be supplied, such as four dNMP or dNDPs that have a fifth fluorophore distinct from the four used to identify the nucleotides. Because these molecules do not contain three phosphate groups, they can enter the polymerase, but they cannot bond covalently. If included in a higher concentration relative to the nucleotide fluorophores, they can provide a specific signal indicating the transition between attachment of one base and the next. Hence the signal from the "counter" nucleotide would usually be received between each actual signal, and serve to indicate that a new actual nucleotide has been added (for example syncopating the addition of three Ts as: T-counter-T-counter-T-counter). Repeat sequencing can be performed to confirm the result, and address the possibility that the counter may not be added or detected in some instances of each sequencing reaction. The counter nucleotides can also provide a means of determining the number of bases in runs of bases. However, important information about sequences can be obtained even without the use of the counter nucleotides, such as a rough approximation of the sequence, or quick confirmation of a sequence obtained by other methods.

Another approach to distinguishing multiple bases of the same type is to incubate the reaction at a low temperature, such as 0-30° C., for example 4° C. or at RT. At these lower temperatures, the polymerases are selected that are able to function properly at lower temperatures. This temperature range allows for a more narrow spectral line and hence higher coding complexity. If more than one fluorescent acceptor is present on each nucleotide, then the individual classes of nucleotides are coded. The lower temperature sharpens the spectrum, allowing more distinct spectra to be read. It is important to avoid freezing, which would interfere with the polymerization reaction. Other approaches to distinguishing multiple bases of the same type include making the aqueous environment 36 more viscous, reducing the concentration of nucleotides, and using a polymerase containing one or more mutations which slow the polymerase.

To help assure that the selected fluorescent nucleotides can be incorporated into a nucleic acid by a polymerase, the fluorescent nucleotides are first tested using a fluorescence spectrophotometer. For example, 5' biotin-labeled single-stranded nucleic acid is attached to magnetic streptavidin particles. A primer is annealed and the polymerase and one or more fluorescent nucleotides are added. After washing the beads, the nucleic acid is cleaved at a restriction site close to the bead. The fluorescence spectrophotometer is used to detect addition of the fluorescent nucleotides. The test can also be performed by separation of the labeled nucleic acids on an agarose gel and detection under UV lamp or using an ABI sequencing machine. Therefore, the contribution of previously incorporated bases to the current spectrum can be determined by accounting for known spectrum of nucleotides at various previous positions. Since the previous sequence is known, the predicted effect of the previous nucleotides can be removed from the current spectrum.

Another method that can be used to distinguish the latest nucleotide added onto the growing nucleotide chain is to use polarized light to measure the rotation of single molecules. In this embodiment, the newly added base is fixed in orientation.

The location of the donor dipole is adjusted to match the most recently added acceptor fluorophore so that the most recent fluorophore generates the strongest FRET signal. Harms et al. teaches the use of polarized light to measure rotation of single molecules (*Biophys. J.* 77:2864-70, 1999, herein incorporated by reference).

Yet another method to distinguish the individual nucleotides is to label the nucleotides with more than one fluorophore. For example, two or more different fluorophores can be added to each nucleotide. The combination of fluorophores generates an emission spectrum which is easier to distinguish than the emission spectrum from only one fluorophore on each nucleotide. Multiple tags thereby allow each nucleotide to be coded by more than one spectrum, helping to reduce the ambiguity of strings of the same nucleotide.

Distinguishing multiple nucleotides of the same type may be difficult because the signal is not synchronized. The resulting sequence, if recorded, would be "compressed". For example, the first 30 bases of an *E. coli* sequence:

(1) agcttttcattctgactgcaacgggcaata (SEQ ID NO: 1)

would be compressed by removing strings of similar bases:

(2) agct cat ctgactgca cg ca ta resulting in:

(3) agctcatctgactgcacgcata    (SEQ ID NO: 2)

Such a compressed sequence is still usable because it is unique. For example, if RNA from *E. coli* is sequenced and results in sequence 3 above, the location of the RNA can be determined. When the entire human genome is sequenced, this method can be used to count individual mRNA molecules directly. The first step is to compress the entire human genomic sequence. Then, the NCBI Basic Local Alignment Search Tool (BLAST), or other program is used to search this compressed human genomic sequence using the results obtained from the sequencing methods of the present disclosure. This method does not require macroscopic handling for high-throughput analysis, and is highly useful for studying gene expression.

BLAST (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

Example 4

Microscope Set-Up

This example describes microscope systems that can be used to sequence nucleic acids using the method disclosed herein.
Microscopes
Total internal reflectance (TIR) fluorescence microscopy can be used, for example using the methods and device described by Pierce et al. (*Nature*, 388:338, 1997; *Methods Cell Biol.* 58:49, 1999); Funatsu et al. (*Nature*, 374:555, 1995); Weiss (*Science*, 283:1676, 1999) and Schutt et al. (U.S. Pat. No. 5,017,009). TIR is an optical phenomenon that occurs when light is directed at less than a critical angle, through a high refractive index material, toward an interface of that material with a second material having a lower refractive index. In this situation, all light is reflected back from that interface, except for a microscopic evanescent wave which propagates into the second material for only a short distance.

In TIR fluorescence microscopy, the first material is a glass substrate and the second material is water or another aqueous medium in which an assay is being conducted. When fluorescently labeled materials approach the interface, within the field of the evanescent wave, the fluorescent molecules can be energized, and fluorescence detected which then emanates into the overlying solution. The advantage of TIR is that it produces a superior signal-to-noise ratio, and reduces the photobleaching of the fluorescent molecules since only a thin layer of the sample is exposed.

To reduce photobleaching of the fluorophores, a confocal microscopy system can be used. An example of such a confocal laser is the Leica Confocal Spectrophotometer TCS-SP (Leica, Germany). The confocal laser would only illuminate sequencing polymerases, leaving the remainder of the reservoir dark. To accomplish this, one can first scan the entire volume available for polymerases, then program the microscope to only expose those small regions containing functioning polymerases. Another advantage of confocal microscopy is that sequencing reactions could occur in three dimensions. Confocal microscopy excludes planes that are not of interest, allowing one to increase the total number of sequences taken. This would allow more sequencing reactions to be performed and detected per field of view.

Another means that can be used to reduce photobleaching is to incubate the sample in a solution containing an oxygen scavenger system, for example as described by Kitamura et al. (*Nature*, 397:129, 1999); Okada and Hirokawa (*Science*, 283:1152, 1999); Harada et al. (*J. Mol. Biol.* 216:49, 1990). Examples of solutions include: 1% glucose, 0.05 mg/ml glucose oxidase and 0.1 mg/ml catalase; and 0.5% 2-mercaptoethanol, 4.5 mg/ml glucose, 216 µg/ml glucose oxidase, 36 µg/ml catalase, 2 mM ATP in buffer.

Near-field scanning optical microscopy (NSOM) may also be used for the sequencing method disclosed herein. Several methods and devices for NSOM have been described in the prior art (U.S. Pat. No. 5,105,305 and PCT Publication WO 97/30366). In NSOM, an aperture having a diameter that is smaller than an optical wavelength is positioned in close proximity (i.e., within less than one wavelength) to the surface of a specimen and scanned over the surface. Light may be either emitted or collected by such an aperture in the end of a probe. Mechanical or piezoelectric means are provided for moving the probe relative to the sample. Light that has interacted with the sample is collected and detected by, for example, a spectrophotometer, and then a CCD camera. The strength of the detected light signal is typically stored, in the form of digital data, as a function of the probe position relative to the sample. The stored data can be converted into a nucleic acid sequence. NSOM allows optical measurements with sub-wavelength resolution, can measure FRET, and works well in solution (Ha et al., *Proc. Natl. Acad. Sci. USA* 93:6264-8, 1996). Standard microscopes can be converted to a near-field optical microscope using a device sold by Nanonics Ltd. (Malha, Jerusalem, Israel).

The advantage of NSOM is that high resolution of the sample can be obtained. However, since the probe scans the surface of the substrate, the number of sequencing reactions that can be monitored at any one time decreases. To help compensate for this decrease, the rate of nucleotide addition can be decreased by increasing the viscosity of the solution or decreasing the temperature.

Kairos Scientific provides a Fluorescence Imaging MicroSpectrophotometer (FIMS). This microscope generates a fluorescence emission spectrum for every pixel in the field of view. Therefore, a unique emission spectrum is generated for each nucleotide as it is added to the complementary nucleic acid strand. In other embodiments, the method allows for single molecule detection (SMD), for example using the system disclosed by Fang and Tan (*Anal. Chem.* 1999, 71:3101-5, herein incorporated by reference). Briefly, in this system an optical fiber is used to probe into a fluorophore solution (i.e. the aqueous environment 36 of FIG. 3), or at a solid surface (i.e. the substrate 12 shown in FIG. 3). The optical fiber has total internal reflection, allowing fluorescent molecules close to the surface to be excited by the evanescent wave. The fluorescent signals generated by the fluorophores are detected by an intensified charge-coupled device (ICCD)-based microscope system. Optical fibers can be purchased from Newport Corp. (Irvine, Calif.).

In yet other embodiments, SMD can be performed using the method disclosed by Unger et al. (*BioTechniques,* 1999, 27:1008-14, herein incorporated by reference). Briefly, using a standard fluorescent microscope with mercury lamp excitation and a CCD camera, single fluorescent molecules can be observed in air and in aqueous solution, if the molecules are sufficiently separated by dilution.

Sources of Electromagnetic Radiation

In particular embodiments, electromagnetic radiation can be emitted by a laser. The choice of laser used will depend on the specific donor fluorophore used. The wavelength of the laser light is selected to excite the donor fluorophore. For example, wild-type GFP and FITC can be excited by an argon laser at 488 nm. To excite the H9-40 GFP mutant, blue laser diodes which emit at 400 nm (Nichia Chemical Industries Ltd.) or 404 nm (Power Technology Inc., Little Rock, Ark.) can be used. Other sources of electromagnetic radiation known by those skilled in the art can also be used, for example HeNe lasers and mercury lamps.

Fluidics

The use of a fluid handling system is optional. For simplicity, one may prefer to add all of the necessary reagents, then seal the chamber with a glass coverslip or a drop of oil to prevent desiccation. Alternatively, a slow flow of nucleotide containing solution can be provided to replenish the nucleotides and to remove the products (diphosphate). Such a system would increase nucleotide use, but would maintain steady state conditions, which may increase the length of sequencing runs.

A computer chip that performs the liquid handling can be built that sits on the stage of a fluorescent microscope. Micromachine and micro fluidic devices and methods for the dispensing of nanoliter size liquid samples has been previously described (Service, *Science* 282:399-401, 1998; Burns et al. *Science* 282:484-7 1998).

Detectors

A detector acts as the primary tool to capture the emission spectrums generated by the spectrophotometer.

A CCD camera can be used as the detector to capture the image. The emission spectrums generated by the spectrophotometer are collected by the CCD camera, which converts this input into a charge. The charge is converted into a signal by the CCD output. The resulting signal is digitized, as a characteristic signal associated with each type of nucleotide (e.g. A, T/U, C or G), and the digital data is captured into memory, such as the hard-drive of a computer. The sum of the captured data is then processed into a nucleotide sequence. CCD cameras are commercially available from many sources including Kodak (Rochester, N.Y.).

With color CCD cameras containing more than 1000 by 1000 pixel fields (for example the Kodak Professional DCS 520 Digital Camera), or even 4096 by 4096 pixel fields (for example the Kodak 16.8i, KAF16800), it is possible to sequence as many as 1000 nucleic acids in parallel, at a rate of 360 bases per hour. Therefore, molecular sequencing with the TDS method has the potential to sequence entire chromosomes or genomes within a day. If the polymerases are placed in a regular hexagonal regular array, about 17 pixels would be available for each polymerase.

Alternatively, a monochrome CCD containing filters or other means of obtaining a spectrum may be used. This would require that the spectrum be swept. To reduce background noise, any of the CCD cameras may be cooled.

The rate at which sequencing of the nucleic acids occurs can be controlled by many factors. Faster rates can be obtained by increasing the temperature (using a heat stable polymerase) or by running the reactions under high pressure, as in HPLC. The reaction rate can be slowed by making the solution more viscous, by lowering the reaction temperature, or by having fewer reactive nucleotides available. The rate of polymerization may be controlled in this manner not to exceed the rate of the CCD integration and computer recording time. Therefore, the rate of polymerization is controlled in this manner such that the fluorescent signal can be more reliably read by the CCD and interpreted by the computer.

In a disclosed embodiment, the method is performed in a closed chamber device that produces sequencing signals, which enter the computer directly. The method sequences nucleic acids by monitoring the incorporation of individual nucleotides into individual nucleic acid molecules on the molecular level, instead of sequencing nucleic acids by monitoring macromolecular events, such as a pattern on an electrophoresis gel, that are representative of a large population of nucleic acids molecules. Once the reaction has started, no further liquid handling is necessary (but can be added if desired). Therefore, the machine has no macroscopic moving parts during operation, which can facilitate rapid sequencing.

As an alternative to a CCD camera, photomultiplier tubes or an intensified charge-coupled device (ICCD) can be used.

Example 5

Computer System

The methods disclosed herein can be performed in the general context of computer-executable instructions of a computer program that runs on a personal computer. Generally, program modules include routines, programs, components, data structures, etc. that perform particular tasks or implement particular abstract data types. Moreover, those skilled in the art will appreciate that the method may be practiced with other computer system configurations, including hand-held devices, multi-processor systems, microprocessor-based or programmable consumer electronics, minicomputers, mainframe computers, and the like. The methods disclosed herein may also be practiced in distributed computing environments where tasks are performed by remote processing devices that are linked through a communications network. In a distributed computing environment, program modules may be located in both local and remote memory storage devices.

The present implementation platform of the methods disclosed herein is a system implemented on a Sun computer having at least one megabyte of main memory and a one gigabyte hard disk drive, with Unix as the user interface. The application software is written in Pascal or other computer language.

Example 6

Sequencing of Nucleic Acids

This example describes methods for sequencing nucleic acids from different sources.

Many different sequences can be determined in parallel. One application of the disclosed method is the sequencing of a plasmid. After introducing random nicks into the plasmid, the DNA is added onto a substrate containing fixed fluorescent polymerases (Examples 1 and 2). The entire plasmid is then sequenced from many points. The computer keeps track of all the sequences and automatically assembles them into a complete plasmid sequence.

Another use is for sequencing a randomized region of a nucleic acid. The primer used is specific for a position just outside the randomized region. The randomized nucleic acid is placed onto the field of fixed polymerases. This method allows one to obtain the entire results of a randomization experiment in parallel, thereby saving time and money.

Nick translation can be used to randomly sequence an unknown nucleic acid.

Example 7

Clinical Applications

This example describes how the methods disclosed herein can be used for the analysis of pathology specimens. The source of specimen obtained from a subject may include peripheral blood, urine, saliva, tissue biopsy, fine needle aspirates, surgical specimen, amniocentesis samples and autopsy material. The sample is attached to a substrate, such as a glass slide. Care must be taken to preserve the nucleic acids present in the sample. Alternatively, the nucleic acids could be isolated from the sample, and then subjected to TDS. For example, one can use the present method to sequence whole bacterial chromosomes and human genes containing mutations. Using techniques described previously, the presence of viral and/or bacterial pathogens can be detected by the presence of the viral and/or bacterial nucleic acid sequences. In addition, the methods disclosed herein allows for nucleic acid sequencing in situ, by adding a primer, the GFP-polymerase (or GFP-aequorin-polymerase) and the four nucleotides, to a thin tissue slice.

In view of the many possible embodiments to which the principles of the present disclosure may be applied, it should be recognized that the illustrated embodiments are only particular examples and should not be taken as a limitation on the scope of the disclosure. Rather, the scope of the disclosure is defined by the following claims. We therefore claim as our invention all that comes within the scope and spirit of these claims.

I claim:

1. A method for high speed parallel molecular nucleic acid sequencing, comprising:
   (a) attaching a nucleic acid molecule to be sequenced to a substrate;
   (b) adding an oligonucleotide primer under conditions where the primer anneals to the nucleic acid molecule;
   (c) adding a green fluorescent protein (GFP)-polymerase and nucleotides, wherein the nucleotides are labeled with a fluorophore, and wherein each type of nucleotide comprises a different fluorophore that emits a unique emission signal corresponding to addition of that type of nucleotide as the nucleotide is incorporated into a complementary nucleic acid molecule by the GFP-polymerase;
   (d) adding four deoxyribonucleoside monophosphates (dNMPs) or deoxyribonucleoside diphosphates (dNDPs), wherein the dNMPs or dNDPs comprise a fluorophore distinct from the fluorophores on the nucleotides; and
   (e) detecting the unique emission signal.

2. The method of claim 1, wherein the unique emission signal is converted into a signal for a specific nucleotide in a nucleic acid sequence.

3. The method of claim 1, wherein the nucleic acid molecule is DNA and the polymerase is a DNA or RNA polymerase.

4. The method of claim 1, wherein the nucleic acid molecule is RNA and the polymerase is reverse transcriptase.

5. The method of claim 1, wherein the polymerase is a Klenow fragment of DNA polymerase I.

6. The method of claim 1, wherein the unique emission signal is generated by fluorescent resonance energy transfer (FRET) or luminescence resonance energy transfer (LRET).

7. The method of claim 1, wherein the fluorophore of each nucleotide is an acceptor fluorophore.

8. The method of claim 1, wherein the GFP is a GFP mutant protein.

9. The method of claim 1, wherein the GFP mutant protein is RSGFP4, BFP5, or H9-40.

10. The method of claim 7, wherein the acceptor fluorophores are 4,4-difluoro-4-bora-3a,4a-diaza-s-indacene, fluorescein, and 2',7'-difluorofluorescein, or tetramethylrhodamine, rhodamine B sulfonyl chloride, sulforhodamine 101 acid chloride and naphthofluorescein.

11. The method of claim 1, wherein the GFP-polymerase is an aequorin-GFP-polymerase.

12. The method of claim 1, further comprising performing a plurality of sequencing reactions substantially simultaneously, and detecting the signals from the plurality of sequencing reactions.

13. The method of claim 12, wherein a plurality of nucleic acid molecules are fixed directly or indirectly to the substrate in a predetermined pattern, and detecting the signal further comprises correlating the signal with a single nucleic acid molecule corresponding to a predetermined position within that pattern.

14. The method of claim 1, wherein the substrate comprises a biocompatible material that is transparent to light.

15. The method of claim 1, further comprising adding an oxygen scavenger system.

16. A method for high speed parallel molecular nucleic acid sequencing, comprising:
(a) attaching a green fluorescent protein (GFP)-polymerase to a substrate;
(b) adding a nucleic acid molecule to be sequenced;
(c) adding a oligonucleotide primer under conditions where the primer anneals to the nucleic acid molecule to be sequenced;
(d) adding nucleotides, wherein the nucleotides are labeled with a fluorophore, and wherein each type of nucleotide comprises a different fluorophore that emits a unique emission signal corresponding to addition of that type of nucleotide as the nucleotide is incorporated into a complementary nucleic acid molecule by the GFP-polymerase;
(e) adding four deoxyribonucleoside monophosphates (dNMPs) or deoxyribonucleoside diphosphates (dNDPs), wherein the dNMPs or dNDPs comprise a fluorophore distinct from the fluorophores on the nucleotides; and
(f) detecting the unique emission signal.

17. The method of claim 16, wherein the GFP-polymerase is attached to the substrate via a histidine, S-tag, or glutathione-S-transferase (GST) linker.

18. The method of claim 16, wherein the GFP-polymerase is a GFP-aequorin-polymerase.

19. The method of claim 16, further comprising adding an oxygen scavenger system.

* * * * *

```
SEQUENCE LISTING

<160> NUMBER OF SEQ ID NOS: 2

<210> SEQ ID NO 1
<211> LENGTH: 30
<212> TYPE: DNA
<213> ORGANISM: Escherichia coli

<400> SEQUENCE: 1
agcttttcat tctgactgca acgggcaata                                           30

<210> SEQ ID NO 2
<211> LENGTH: 22
<212> TYPE: DNA
<213> ORGANISM: Artificial sequence
<220> FEATURE:
<223> OTHER INFORMATION: Compressed sequence

<400> SEQUENCE: 2
agctcatctg actgcacgca ta                                                   22
```